US011908566B2

(12) United States Patent
Roh et al.

(10) Patent No.: US 11,908,566 B2
(45) Date of Patent: Feb. 20, 2024

(54) EDGE COMPUTING FOR ROBOTIC TELESURGERY USING ARTIFICIAL INTELLIGENCE

(71) Applicant: IX Innovation LLC, Seattle, WA (US)

(72) Inventors: Jeffrey Roh, Seattle, WA (US); Justin Esterberg, Mesa, AZ (US); John Cronin, Jericho, VT (US); Seth Cronin, Essex Junction, VT (US); Michael John Baker, Georgia, VT (US)

(73) Assignee: IX Innovation LLC, Seattle, WA (US)

( * ) Notice: Subject to any disclaimer, the term of this patent is extended or adjusted under 35 U.S.C. 154(b) by 0 days.

(21) Appl. No.: 17/742,206

(22) Filed: May 11, 2022

(65) Prior Publication Data
US 2023/0368887 A1    Nov. 16, 2023

(51) Int. Cl.
*G16H 20/40* (2018.01)
*G05B 19/4155* (2006.01)
*G06N 20/00* (2019.01)
*G16H 40/67* (2018.01)

(52) U.S. Cl.
CPC ......... *G16H 20/40* (2018.01); *G05B 19/4155* (2013.01); *G06N 20/00* (2019.01); *G16H 40/67* (2018.01); *G05B 2219/40269* (2013.01); *G05B 2219/45123* (2013.01)

(58) Field of Classification Search
USPC .......................................................... 705/2
See application file for complete search history.

(56) References Cited

U.S. PATENT DOCUMENTS

| 2006/0074422 A1* | 4/2006 | Story .................. A61L 31/14 606/232 |
| 2019/0183591 A1* | 6/2019 | Johnson ................ G16H 20/40 |
| 2019/0201081 A1* | 7/2019 | Shelton, IV ....... A61B 18/1445 |
| 2021/0090736 A1* | 3/2021 | Innanje ................. G16H 40/63 |
| 2021/0251577 A1* | 8/2021 | Itu .......................... A61B 6/504 |

(Continued)

OTHER PUBLICATIONS

Sankaran, N. K. (2020). Design and development of systems and methods for interventional surgical robot (Order No. 28830012). Available from ProQuest Dissertations and Theses Professional. (2593659015). Retrieved from https://dialog.proquest.com/professional/docview/2593659015?accountid=131444 (Year: 2020).*

*Primary Examiner* — Christopher L Gilligan
*Assistant Examiner* — Bennett Stephen Erickson
(74) *Attorney, Agent, or Firm* — Perkins Coie LLP

(57) ABSTRACT

Methods, apparatuses, and systems for edge computing for robotic telesurgery using artificial intelligence are disclosed. A robotic surgical system includes surgery equipment and can communicate via a cloud network. The system can include operation room (OR) equipment and a surgical computer. The surgical computer transfers data between a remote surgeon, the OR equipment, and the surgery equipment. The surgical computer receives, using the OR equipment and the surgery equipment, data related to a surgical procedure. The data is related to the surgical procedure and is computed using artificial intelligence (AI). The surgical computer determines a risk assessment based on data related to the surgery equipment. The surgical computer sends an indication of the determined risk assessment to the remote surgeon.

21 Claims, 14 Drawing Sheets

(56) References Cited

U.S. PATENT DOCUMENTS

2022/0134537 A1* 5/2022 Chadalavada Vijay Kumar ......... B25J 9/023 700/250
2022/0258334 A1* 8/2022 Krishnamoorthy .......................... G05B 13/0265

* cited by examiner

| SURGICAL EQUIPMENT DATABASE | | | | |
|---|---|---|---|---|
| TOOL | SPEED | TORQUE | TEMPERATURE | FORCE |
| Surgical Drill 1 | 500 rpm | 67.2 ± 8.4 Newton millimeter (N mm) | 34.2 degree Celsius | 2 N |
| Surgical Drill 2 | 450 rpm | 43.4 ± 6.3 Newton millimeter (N mm) | 42.6 degree Celsius | 2.2 N |
| Surgical Drill 3 | 560 rpm | 82.7 ± 3.7 Newton millimeter (N mm) | 39.1 degree Celsius | 2.5 N |
| Spinal Surgery Robotic Arm Inserter – 1 | -- | 7.2 ± 8 Newton millimeter (N mm) | 31.9 degree Celsius | 9.8 N |
| Spinal Surgery Robotic Arm Inserter - 2 | -- | 8.34 ± 2.7 Newton millimeter (N mm) | 33.2 degree Celsius | 10.4 N |

*FIG. 7*

EDGE COMPUTING DATABASE

| TOOL | SENSOR DATA | RISK IDENTIFIED | RECOMMENDATION |
|---|---|---|---|
| Surgical Drill 1 | Image of Alex's spine at 7th thoracic vertebra (T7) | Screw to be inserted may touch the 8th thoracic vertebra (T8), causing pain to Alex | Insert a shorter screw |
| Surgical Drill 2 | Image of Alex's spine at 8th thoracic vertebra (T8) | Screw to be inserted may touch the 9th thoracic vertebra (T9), causing pain to Alex | Insert a shorter screw |
| Surgical Drill 3 | Image of Alex's spine at 9th thoracic vertebra (T9) | Screw to be inserted may touch the 8th thoracic vertebra (T8), causing pain to Alex | Insert a shorter screw |
| Spinal Surgery Robotic Arm Inserter – 1 | Image of Alex's spine | Rod to be inserted may be dislocated by 0.01 cm to left of desired location | Correction during insertion of rod, recalibrate the robotic arm inserter |
| Spinal Surgery Robotic Arm Inserter - 2 | Image of Alex's spine | Rod to be inserted may be dislocated by 0.2 cm to left of desired location | Correction during insertion of rod, recalibrate the robotic arm inserter |

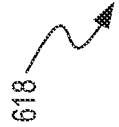

FIG. 8

EDGE COMPUTING FOR ROBOTIC TELESURGERY USING ARTIFICIAL INTELLIGENCE

TECHNICAL FIELD

The present disclosure is generally related to automated and robotic surgical procedures and specifically to methods and systems for edge computing for robotic telesurgery using artificial intelligence.

BACKGROUND

More than 200 million surgeries are performed worldwide each year, and recent reports reveal that adverse event rates for surgical conditions remain unacceptably high, despite traditional patient safety initiatives. Adverse events resulting from surgical interventions can be related to errors occurring before or after the procedure as well as technical surgical errors during the operation. For example, adverse events can occur due to (i) breakdown in communication within and among the surgical team, care providers, patients, and their families; (ii) delay in diagnosis or failure to diagnose; and (iii) delay in treatment or failure to treat. The risk of complications during surgery can include anesthesia complications, hemorrhaging, high blood pressure, a rise or fall in body temperature, etc. Such adverse events can further occur due to medical errors, infections, underlying physical or health conditions of the patient, reactions to anesthetics or other drugs, etc. Conventional methods for preventing wrong-site, wrong-person, wrong-procedure errors, or retained foreign objects are typically based on communication between the patient, the surgeon(s), and other members of the health care team. However, conventional methods are typically insufficient to prevent surgical errors and adverse events during surgery.

BRIEF DESCRIPTION OF THE DRAWINGS

FIG. 7 illustrates a structure of an example surgical equipment database for edge computing for robotic telesurgery using artificial intelligence, in accordance with one or more embodiments.

FIG. 8 illustrates a structure of an example edge computing database for edge computing for robotic telesurgery using artificial intelligence, in accordance with one or more embodiments.

DETAILED DESCRIPTION

Figure 1:
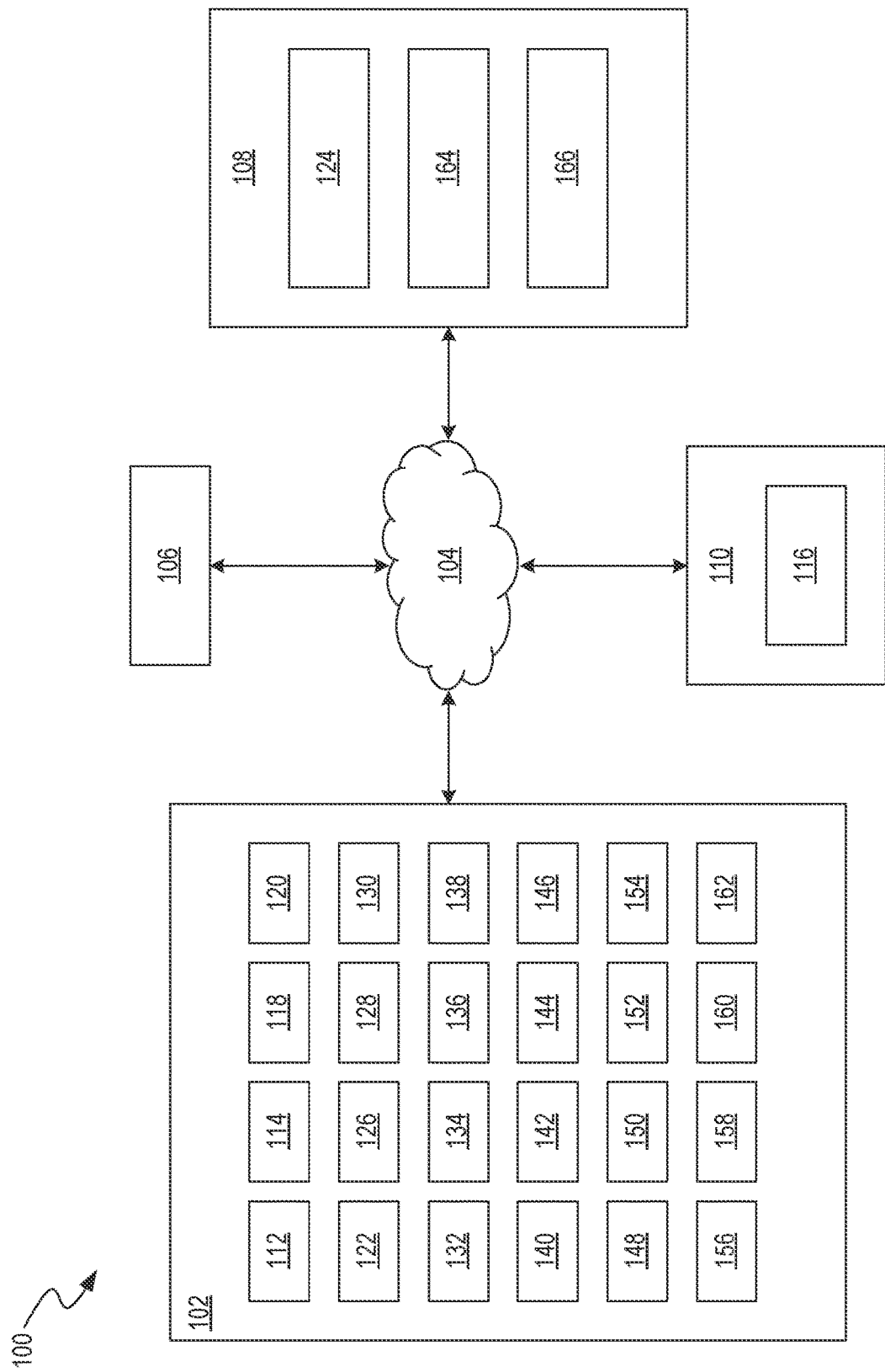
FIG. 1 is a block diagram illustrating an example surgical system, in accordance with one or more embodiments.

Embodiments of the present disclosure will be described more thoroughly from now on with reference to the accompanying drawings. Like numerals represent like elements throughout the several figures, and in which example embodiments are shown. However, embodiments of the claims can be embodied in many different forms and should not be construed as limited to the embodiments set forth herein. The examples set forth herein are non-limiting examples and are merely examples, among other possible examples. Throughout this specification, plural instances (e.g., "610") can implement components, operations, or structures (e.g., "610a") described as a single instance. Further, plural instances (e.g., "610") refer collectively to a set of components, operations, or structures (e.g., "610a") described as a single instance. The description of a single component (e.g., "610a") applies equally to a like-numbered component (e.g., "610b") unless indicated otherwise. These and other aspects, features, and implementations can be expressed as methods, apparatus, systems, components, program products, means or steps for performing a function, and in other ways. These and other aspects, features, and implementations will become apparent from the following descriptions, including the claims.

The embodiments for robotic telesurgery described herein can be used to provide healthcare surgical services to patients at remote locations. For example, the methods disclosed herein can be used by a surgeon at a master facility to perform surgery by guiding a surgical robot at a surgical facility. The surgeon at the master facility can control the surgery by sending control commands to the surgical facility using a system interface including haptic devices, headphones, or video consoles for audio-video feedback. Traditional surgical approaches sometimes fail due to high communication latencies and overheads, which limit the applicability and reliability of traditional systems. Communication overhead can consume much bandwidth and limit surgical procedures. Further, latency times generally define a delay time in transferring auditory, visual, or tactile feedback between two locations. High communication latency can be attributed to server overload, network routing problems, and congestion. Time delays not only lengthen surgical procedures but also lead to surgical inaccuracies and unreliability, which can risk the safety of the patient. A surgical robot can use the embodiments described herein to determine whether to perform at least a portion of a surgical procedure on-the-edge or perform one or more edge computing processes based on whether a network connection is available, latency times of a network, data speeds over the network, stability of communication channels, or the like. If an adverse communication event (e.g., excess latency times, data speeds below a threshold, etc.) is identified, the surgical robot can use edge computing to perform one or more surgical actions according to a surgical plan. In this manner, robotic telesurgery can be performed independent of adverse communication events.

The embodiments disclosed herein describe methods, apparatuses, and systems using edge computing and artificial intelligence for robotic telesurgery. In some embodiments, a surgical robot for performing robotic telesurgery using edge computing includes sensors configured to measure a speed of the surgical robot and capture images of a surgical site of the robotic telesurgery. An edge computing system is communicably coupled to the sensors and includes an artificial intelligence (AI) accelerator configured to receive the speed and the images. A machine learning (ML) model operates on the AI accelerator and is trained to generate a prediction of an adverse surgical event based on the speed and the images. The ML model is used to generate instructions for controlling the surgical robot to avoid the adverse surgical event. A robotic arm is communicably coupled to the edge computing system and includes robotic links and robotic joints configured to move the robotic links to perform the robotic telesurgery. The robotic arm has a number of degrees of freedom corresponding to a number of the robotic joints. The number of degrees of freedom enable the robotic arm to move to a spatial position and an orientation. The surgical robot is configured to position the robotic arm in a first configuration to perform the robotic telesurgery. The first configuration is defined by the spatial position and the orientation. The robotic arm is moved to a second configuration based on the instructions. An end effector is configured to perform at least one action to avoid the adverse event when the robotic arm is positioned in the second configuration.

The advantages and benefits of the methods, systems, and apparatus disclosed herein include compatibility with best practice guidelines for performing surgery in an operating room, e.g., from regulatory bodies and professional standards organizations such as the Association for Surgical Technologists. The robotic surgical system disclosed uses computer networks, the Internet, intranets, and supporting technologies to implement a cost-effective technology to collect, transmit, store, analyze, and use surgical information in electronic formats. As a result, surgical robots can use the embodiments to collect and analyze vast amounts of information, resulting in early diagnoses. The robotic telesurgery system disclosed herein provides a significant societal impact by addressing a shortage of surgeons and also eliminates geographical barriers to providing timely and high-quality surgical interventions. The robotic telesurgery system helps prevent complications, reduces the financial burden, and obviates often-risky long-distance travel. Further, the telesurgery system provides benefits not only to patients but also to surgeons by ensuring their safety.

The embodiments disclosed herein provide numerous technological advancements, such as edge computing that improve accuracy and reliability. The disclosed methods move processing of the data closer to the surgical site and address the disadvantages associated with latency time. Using the edge computing embodiments at a surgical facility enables operation room (OR) equipment to continue to operate even in critical conditions when there are delays in communicating with a remote surgeon. The use of edge computing mitigates limitations of bandwidth and latencies of connection to a centralized processor. Further, the surgical robot disclosed herein improves the robotic telesurgery reliability, security, and cost-effectiveness.

The robotic surgery technologies disclosed further offer valuable enhancements to medical or surgical processes through improved precision, stability, and dexterity. The disclosed methods make medical procedures safer and less costly for patients. The embodiments disclosed enable more accurate surgery to be performed in more minute locations on or within the human body. The embodiments also address the use of dangerous substances. The adoption of robotic systems, according to the embodiments disclosed herein, provides several additional benefits, including efficiency and speed improvements, lower costs, and higher accuracy. The equipment tracking system integrated into the disclosed embodiments offers flexibility and other advantages, such as requiring no line-of-sight, reading multiple radio frequency identification (RFID) objects at once, and scanning at a distance. The advantages offered by the surgical tower according to the embodiments disclosed herein are smaller incisions, less pain, lower risk of infection, shorter hospital stays, quicker recovery time, less scarring, and reduced blood loss. The advantages of the convolutional neural network (CNN) used for machine learning (ML) in the disclosed embodiments include the obviation of feature extraction and the use of shared weight in convolutional layers, which means that the same filter (weights bank) is used for each node in the layer; this both reduces memory footprint and improves performance.

FIG. 1 is a block diagram illustrating an example surgical system 100, in accordance with one or more embodiments. The system 100 includes various surgical and medical equipment (e.g., a patient monitor 112) located within an operating room 102 or a doctor's office 110, a console 108 for performing surgery or other patient care, and a database 106 for storing electronic health records. The console 108 is the same as or similar to the console 420 illustrated and described in more detail with reference to FIG. 4A. The system 100 is implemented using the components of the example computer system 300 illustrated and described in more detail with reference to FIG. 3. Likewise, embodiments of the system 100 can include different and/or additional components or can be connected in different ways.

The operating room 102 is a facility, e.g., within a hospital, where surgical operations are carried out in an aseptic environment. Proper surgical procedures require a sterile field. In some embodiments, the sterile field is maintained in the operating room 102 in a medical care facility such as a hospital, the doctor's office 110, or outpatient surgery center.

In some embodiments, the system 100 includes one or more medical or surgical patient monitors 112. The monitors 112 can include a vital signs monitor (a medical diagnostic instrument), which can be a portable, battery powered, multi-parametric, vital signs monitoring device used for both ambulatory and transport applications as well as bedside monitoring. The vital signs monitor can be used with an isolated data link to an interconnected portable computer or the console 108, allowing snapshot and trended data from the vital signs monitor to be printed automatically at the console 108, and also allowing default configuration settings to be downloaded to the vital signs monitor. The vital signs monitor is capable of use as a stand-alone unit as well as part of a bi-directional wireless communications network that includes at least one remote monitoring station (e.g., the console 108). The vital signs monitor can measure multiple physiological parameters of a patient wherein various sensor output signals are transmitted either wirelessly or by means of a wired connection to at least one remote facility, such as the console 108.

In some embodiments, the monitors 112 include a heart rate monitor, which is a sensor and/or a sensor system applied in the context of monitoring heart rates. The heart rate monitor measures, directly or indirectly, any physiological condition from which any relevant aspect of heart rate can be gleaned. For example, some embodiments of the heart rate monitor measure different or overlapping physiological conditions to measure the same aspect of heart rate. Alternatively, some embodiments measure the same, different, or overlapping physiological conditions to measure different aspects of heart rate, e.g., number of beats, strength of beats, regularity of beats, beat anomalies, etc.

In some embodiments, the monitors 112 include a pulse oximeter or SpO2 monitor, which is a plethysmograph or any instrument that measures variations in the size of an organ or body part of the patient on the basis of the amount of blood passing through or present in the part. The pulse oximeter is a type of plethysmograph that determines the oxygen saturation of the blood by indirectly measuring the oxygen saturation of the patient's blood (as opposed to measuring oxygen saturation directly through a blood sample) and changes in blood volume in the skin. The pulse oximeter can include a light sensor that is placed at a site on the patient, usually a fingertip, toe, forehead, or earlobe, or in the case of a neonate, across a foot. Light, which can be produced by a light source integrated into the pulse oximeter, containing both red and infrared wavelengths, is directed onto the skin of the patient, and the light that passes through the skin is detected by the pulse oximeter. The intensity of light in each wavelength is measured by the pulse oximeter over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation.

In some embodiments, the monitors 112 include an end tidal CO2 monitor or capnography monitor used for measurement of the level of carbon dioxide that is released at the end of an exhaled breath (referred to as end tidal carbon dioxide, ETCO2). An end tidal CO2 monitor or capnography monitor is widely used in anesthesia and intensive care. ETCO2 can be calculated by plotting expiratory CO2 with time. Further, ETCO2 monitors are important for the measurement of applications such as cardiopulmonary resuscitation (CPR), airway assessment, procedural sedation and analgesia, pulmonary diseases such as obstructive pulmonary disease, pulmonary embolism, etc., heart failure, metabolic disorders, etc. The end tidal CO2 monitor can be configured as side stream (diverting) or mainstream (non-diverting). A diverting end tidal CO2 monitor transports a portion of a patient's respired gases from the sampling facility to the end tidal CO2 monitor while a non-diverting end tidal CO2 monitor does not transport gas away. Also, measurement by the end tidal CO2 monitor is based on the absorption of infrared light by carbon dioxide where exhaled gas passes through a sampling chamber containing an infrared light source and photodetector on both sides. Based on the amount of infrared light reaching the photodetector, the amount of carbon dioxide present in the gas can be determined.

In some embodiments, the monitors 112 include a blood pressure monitor that measures blood pressure, particularly in arteries. The blood pressure monitor uses a non-invasive technique (by external cuff application) or an invasive technique (by a cannula needle inserted in artery, used in the operating room 102) for measurement. The non-invasive method (referred to as a sphygmomanometer) works by measurement of force exerted against arterial walls during (i) ventricular systole (i.e., systolic blood pressure occurs when the heart beats and pushes blood through the arteries) and (ii) ventricular diastole (i.e., diastolic blood pressure occurs when the heart rests and is filling with blood) thereby measuring systole and diastole, respectively. The blood pressure monitor can be of three types: automatic/digital, manual (aneroid-dial), and manual (mercury-column). The sphygmomanometer can include a bladder, a cuff, a pressure meter, a stethoscope, a valve, and a bulb. The cuff inflates until it fits tightly around the patient's arm, cutting off the blood flow, and then the valve opens to deflate it. The blood pressure monitor operates by inflating a cuff tightly around the arm; as the cuff reaches the systolic pressure, blood begins to flow in the artery, creating a vibration, which is detected by the blood pressure monitor, which records the systolic pressure. The techniques used for measurement can be auscultatory or oscillometric.

In some embodiments, the monitors 112 include a body temperature monitor. The body temperature monitor measures the temperature invasively or non-invasively by placement of a sensor into organs such as bladder, rectum, esophagus, tympanum, etc., and mouth, armpit, etc., respectively. The body temperature monitor is of two types: contact and non-contact. Temperature can be measured in two forms: core temperature and peripheral temperature. Temperature measurement can be done by thermocouples, resistive temperature devices (RTDs, thermistors), infrared radiators, bimetallic devices, liquid expansion devices, molecular change-of-state, and silicon diodes. A body temperature monitor commonly used for the measurement of temperature includes a temperature sensing element (e.g., temperature sensor) and a means for converting to a numerical value.

In some embodiments, the monitors 112 measure respiration rate or breathing rate—the rate at which breathing occurs—and which is measured by the number of breaths the patient takes per minute. The rate is measured when a person is at rest and simply involves counting the number of breaths for one minute by counting how many times the chest rises. Normal respiration rates for an adult patient at rest are in the range: 12 to 16 breaths per minute. A variation can be an indication of an abnormality/medical condition or the patient's demographic parameters. The monitors 112 can indicate hypoxia, a condition with low levels of oxygen in the cells, or hypercapnia, a condition in which high levels of carbon dioxide are in the bloodstream. Pulmonary disorders, asthma, anxiety, pneumonia, heart diseases, dehydration, and drug overdose are some abnormal conditions, which can cause a change to the respiration rate, thereby increasing or reducing the respiration rate from normal levels.

In some embodiments, the monitors 112 measure an electrocardiogram (EKG or ECG), a representation of the electrical activity of the heart (graphical trace of voltage versus time) by placement of electrodes on skin/body surface. The electrodes capture the electrical impulse, which travels through the heart causing systole and diastole or the pumping of the heart. This impulse provides information related to the normal functioning of the heart and the production of impulses. A change can occur due to medical conditions such as arrhythmias (tachycardia, where the heart rate becomes faster, and bradycardia, where the heart rate becomes slower), coronary heart disease, heart attacks, or cardiomyopathy. The instrument used for measurement of the electrocardiogram is called an electrocardiograph, which measures the electrical impulses by the placement of electrodes on the surface of the body and represents the ECG by a PQRST waveform. A PQRST wave is read as: P wave, which represents the depolarization of the left and right atrium and corresponds to atrial contraction; QRS complex, which indicates ventricular depolarization and represents the electrical impulse as it spreads through the ventricles; and T wave, which indicates ventricular repolarization and follows the QRS complex.

In some embodiments, the monitors 112 perform neuromonitoring, also called intraoperative neurophysiological monitoring (IONM). For example, the monitors 112 assess functions and changes in the brain, brainstem, spinal cord, cranial nerves, and peripheral nerves during a surgical procedure on these organs. Monitoring includes both continuous monitoring of neural tissue as well as the localization of vital neural structures. IONM measures changes in these organs where the changes are indicative of irreversible damage or injuries in the organs, aiming at reducing the risk of neurological deficits after operations involving the nervous system. Monitoring is effective in localization of anatomical structures, including peripheral nerves and the sensorimotor cortex, which helps in guiding a surgical robot during dissection. Electrophysiological modalities employed in neuromonitoring are an extracellular single unit and local field recordings (LFP), somatosensory evoked potential (SSEP), transcranial electrical motor evoked potentials (TCeMEP), electromyography (EMG), electroencephalography (EEG), and auditory brainstem response (ABR). The use of neurophysiological monitoring during surgical procedures requires anesthesia techniques to avoid interference and signal alteration due to anesthesia.

In some embodiments, the monitors 112 measure motor evoked potential (MEP), electrical signals that are recorded from descending motor pathways or muscles following stimulation of motor pathways within the brain. MEP is determined by measurement of the action potential elicited by non-invasive stimulation of the motor cortex through the scalp. MEP is for intraoperative monitoring and neurophysiological testing of the motor pathways specifically during spinal procedures. The technique of monitoring for measurement of MEP is defined based on parameters, such as a site of stimulation (motor cortex or spinal cord), method of stimulation (electrical potential or magnetic field), and site of recording (spinal cord or peripheral mixed nerve and muscle). The target site is stimulated by the use of electrical or magnetic means.

In some embodiments, the monitors 112 measure somatosensory evoked potential (SSEP or SEP): the electrical signals generated by the brain and the spinal cord in response to sensory stimulus or touch. SSEP is used for intraoperative neurophysiological monitoring in spinal surgeries. The measurements are reliable, which allows for continuous monitoring during a surgical procedure. The sensor stimulus commonly given to the organs can be auditory, visual, or somatosensory SEPs and applied on the skin, peripheral nerves of the upper limbs, lower limbs, or scalp. The stimulation technique can be mechanical, electrical (provides larger and more robust responses), or intraoperative spinal monitoring modality.

In some embodiments, the monitors 112 provide electromyography (EMG): the evaluation and recording of electrical signals or electrical activity of the skeletal muscles. An electromyography instrument, electromyograph, or electromyogram for the measurement of the EMG activity records electrical activity produced by skeletal muscles and evaluates the functional integrity of individual nerves. The nerves monitored by an EMG instrument can be intracranial, spinal, or peripheral nerves. The electrodes used for the acquisition of signals can be invasive or non-invasive electrodes. The technique used for measurement can be spontaneous or triggered. Spontaneous EMG refers to the recording of myoelectric signals such as compression, stretching, or pulling of nerves during surgical manipulation Spontaneous EMG is recorded by the insertion of a needle electrode. Triggered EMG refers to the recording of myoelectric signals during stimulation of a target site such as a pedicle screw with incremental current intensities.

In some embodiments, the monitors 112 provide electroencephalography (EEG), measuring the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp, where each pair of electrodes transmits a signal to one or more recording channels. EEG is a modality for intraoperative neurophysiological monitoring and assessing cortical perfusion and oxygenation during a variety of vascular, cardiac, and neurosurgical procedures. The waves produced by EEG are alpha, beta, theta, and delta.

In some embodiments, the monitors 112 include sensors, such as microphones or optical sensors, that produce images or video captured from at least one of multiple imaging devices, for example, cameras attached to manipulators or end effectors, cameras mounted to the ceiling or other surface above the surgical theater, or cameras mounted on a tripod or other independent mounting device. In some embodiments, the cameras are body worn by a surgical robot or other surgical staff, cameras are incorporated into a wearable device, such as an augmented reality device like Google Glass™, or cameras are integrated into an endoscopic, microscopic, or laparoscopic device. In some embodiments, a camera or other imaging device (e.g., ultrasound) present in the operating room 102 is associated with one or more areas in the operating room 102. The sensors can be associated with measuring a specific parameter of the patient, such as respiratory rate, blood pressure, blood oxygen level, heart rate, etc.

In some embodiments, the system 100 includes a medical visualization apparatus 114 used for visualization and analysis of objects (preferably three-dimensional (3D) objects) in the operating room 102. The medical visualization apparatus 114 provides the selection of points at surfaces, selection of a region of interest, or selection of objects. The medical visualization apparatus 114 can also be used for diagnosis, treatment planning, intraoperative support, documentation, or educational purposes. The medical visualization apparatus 114 can further include microscopes, endoscopes/arthroscopes/laparoscopes, fiber optics, surgical lights, high-definition monitors, operating room cameras, etc. Three-dimensional (3D) visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times.

In some embodiments, the system 100 includes an instrument 118 such as an endoscope, arthroscope, or laparoscope for minimally invasive surgery (MIS), in which procedures are performed by cutting a minimal incision in the body. An endoscope refers to an instrument used to visualize, diagnose, and treat problems inside hollow organs where the instrument is inserted through natural body openings such as the mouth or anus. An endoscope can perform a procedure as follows: a scope with a tiny camera attached to a long, thin tube is inserted. A surgical robot moves it through a body passageway or opening to see inside an organ. It can be used for diagnosis and surgery (such as for removing polyps from the colon). An arthroscope refers to an instrument used to visualize, diagnose, and treat problems inside a joint by a TV camera inserted through small portals/incisions and to perform procedures on cartilage, ligaments, tendons, etc. An arthroscope can perform the procedure as follows: a surgical robot makes a small incision in a patient's skin and inserts a pencil-sized instrument with a small lens and lighting system to magnify the target site (joint) and viewing of the interior of the joint by means of a miniature TV camera and then performs the procedure. A laparoscope refers to an instrument used to visualize, diagnose, and treat problems inside soft organs like the abdomen and pelvis by a TV camera inserted through small portals/incisions and to perform procedures.

In some embodiments, the system 100 includes fiber optics 120, which refer to flexible, transparent fiber made by drawing glass (silica) or plastic to a diameter slightly thicker than that of a human hair. Fiber optics 120 are arranged in bundles called optical cables and used to transmit light signals across long distances. Fiber optics 120 are used most often as a means to transmit light between the two ends of the fiber and find wide usage in the medical field. Traditional surgery requires sizable and invasive incisions to expose internal organs and operate on affected areas, but with fiber optics 120 much smaller surgical incisions can be performed. Fiber optics 120 contain components such as a core, cladding, and buffer coating. Fiber optics 120 can be inserted in hypodermic needles and catheters, endoscopes, operation theater tools, ophthalmological tools, and dentistry tools. Fiber optic sensors include a light source, optical fiber, external transducer, and photodetector. Fiber optic sensors can be intrinsic or extrinsic. Fiber optic sensors can be categorized into four types: physical, imaging, chemical, and biological.

In some embodiments, the system 100 includes surgical lights 122 (referred to as operating lights) that perform illumination of a local area or cavity of the patient. Surgical lights 122 play an important role in illumination before, during, and after a medical procedure. Surgical lights 122 can be categorized by lamp type as conventional (incandescent) and LED (light-emitting diode). Surgical lights 122 can be categorized by mounting configuration as ceiling-mounted, wall-mounted, or floor stand. Surgical lights 122 can be categorized by type as tungsten, quartz, xenon halogens, and/or LEDs. Surgical lights 122 include sterilizable handles, which allow a surgical robot to adjust light positions. Some important factors affecting surgical lights 122 can be illumination, shadow management (cast shadows and contour shadows), the volume of light, heat management, or fail-safe surgical lighting.

In some embodiments, the system 100 includes a surgical tower 128, e.g., used in conjunction with the robotic surgical system 160 disclosed herein, for MIS. The surgical tower 128 includes instruments used for performing MIS or surgery, which is performed by creating small incisions in the body. The instruments are also referred to as minimally invasive devices or minimally invasive access devices. The procedure of performing MIS can also be referred to as a minimally invasive procedure. MIS is a safer, less invasive, and more precise surgical procedure. Some medical procedures where the surgical tower 128 is useful and widely used are procedures for lung, gynecological, head and neck, heart, and urological conditions. MIS can be robotic or non-robotic/endoscopic. MIS can include endoscopic, laparoscopic, arthroscopic, natural orifice intraluminal, and natural orifice transluminal procedures. A surgical tower access device can also be designed as an outer sleeve and an inner sleeve that telescopingly or slidably engage with one another. When a telescope is used to operate on the abdomen, the procedure is called laparoscopy. The surgical tower 128 typically includes access to a variety of surgical tools, such as for electrocautery, radiofrequency, lasers, sensors, etc.

In some embodiments, radiofrequency (RF) is used in association with MIS devices. The RF can be used for the treatment of skin by delivering it to the skin through a minimally invasive surgical tool (e.g., fine needles), which does not require skin excision. The RF can be used for real-time tracking of MIS devices such as laparoscopic instruments. The RF can provide radiofrequency ablation to a patient suffering from atrial fibrillation through smaller incisions made between the ribs. The RF can be used to perform an endoscopic surgery on the body such as the spine by delivery of RF energy.

In some embodiments, the system 100 includes an instrument 130 to perform electrocautery for burning a part of the body to remove or close off a part of it. Various physiological conditions or surgical procedures require the removal of body tissues and organs, a consequence of which is bleeding. In order to achieve hemostasis and for removing and sealing all blood vessels that are supplied to an organ after surgical incision, the electrocautery instrument 130 can be used. For example, after removing part of the liver for removal of a tumor, etc., blood vessels in the liver must be sealed individually. The electrocautery instrument 130 can be used for sealing living tissue such as arteries, veins, lymph nodes, nerves, fats, ligaments, and other soft tissue structures. The electrocautery instrument 130 can be used in applications such as surgery, tumor removal, nasal treatment, or wart removal. Electrocautery can operate in two modes, monopolar or bipolar. The electrocautery instrument can 130 consist of a generator, a handpiece, and one or more electrodes.

In some embodiments, the system 100 includes a laser 132 used in association with MIS devices. The laser 132 can be used in MIS with an endoscope. The laser 132 is attached to the distal end of the endoscope and steered at high speed by producing higher incision quality than with existing surgical tools thereby minimizing damage to surrounding tissue. The laser 132 can be used to perform MIS using a laparoscope in the lower and upper gastrointestinal tract, eye, nose, and throat. The laser 132 is used in MIS to ablate soft tissues, such as a herniated spinal disc bulge.

In some embodiments, sensors 134 are used in association with MIS devices and the robotic surgical system 160 described herein. The sensors 134 can be used in MIS for tactile sensing of surgical tool-tissue interaction forces. During MIS, the field of view and workspace of surgical tools are compromised due to the indirect access to the anatomy and lack of surgeon's hand-eye coordination. The sensors 134 provide a tactile sensation to the surgeon by providing information regarding shape, stiffness, and texture of organ or tissue (different characteristics) to the surgeon's hands through a sense of touch. This detects a tumor through palpation, which exhibits a "tougher" feel than that of healthy soft tissue, pulse felt from blood vessels, and abnormal lesions. The sensors 134 can output shape, size, pressure, softness, composition, temperature, vibration, shear, and normal forces. The sensors 134 can be electrical or optical, consisting of capacitive, inductive, piezoelectric, piezoresistive, magnetic, and auditory. The sensors 134 can be used in robotic or laparoscopic surgery, palpation, biopsy, heart ablation, and valvuloplasty.

In some embodiments, the system 100 includes an imaging system 136 (instruments are used for the creation of images and visualization of the interior of a human body for diagnostic and treatment purposes). The imaging system 136 is used in different medical settings and can help in the screening of health conditions, diagnosing causes of symptoms, or monitoring of health conditions. The imaging system 136 can include various imaging techniques such as X-ray, fluoroscopy, magnetic resonance imaging (MRI), ultrasound, endoscopy, elastography, tactile imaging, thermography, medical photography, and nuclear medicine, e.g., positron emission tomography (PET). Some factors which can drive the market are cost and clinical advantages of medical imaging modalities, a rising share of ageing populations, increasing prevalence of cardiovascular or lifestyle diseases, and increasing demand from emerging economies.

In some embodiments, the imaging system 136 includes X-ray medical imaging instruments that use X-ray radiation (i.e., X-ray range in the electromagnetic radiation spectrum) for the creation of images of the interior of the human body for diagnostic and treatment purposes. An X-ray instrument is also referred to as an X-ray generator. It is a non-invasive instrument based on different absorption of X-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type and densities of tissue the X-rays pass through. Some of the applications where X-rays are used can be bone fractures, infections, calcification, tumors, arthritis, blood vessel blockages, digestive problems, or heart problems. The X-ray instrument can consist of components such as an X-ray tube, operating console, collimator, grid, detector, radiographic film, etc.

In some embodiments, the imaging system 136 includes MRI medical imaging instruments that use powerful magnets for the creation of images of the interior of the human body for diagnostic and treatment purposes. Some of the applications where MRI can be used can be brain/spinal cord anomalies, tumors in the body, breast cancer screening, joint injuries, uterine/pelvic pain detection, or heart problems. For the creation of the image by an MRI instrument, magnetic resonance is produced by powerful magnets, which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field and energy release is dependent on environmental factors and the chemical nature of the molecules. MRI is more widely suitable for imaging of non-bony parts or soft tissues of the body. MRI can be less harmful as it does not use damaging ionizing radiation as in the X-ray instrument. MRI instruments can consist of magnets, gradients, radiofrequency systems, or computer control systems. Some areas where imaging by MRI should be prohibited can be people with implants.

In some embodiments, the imaging system 136 uses computed tomography imaging (CT) that uses an X-ray radiation (i.e., X-ray range in the electromagnetic radiation spectrum) for the creation of cross-sectional images of the interior of the human body. CT refers to a computerized X-ray imaging procedure in which a narrow beam of X-rays is aimed at a patient and quickly rotated around the body, producing signals that are processed by the machine's computer to generate cross-sectional images—or "slices"—of the body. A CT instrument is different from an X-ray instrument as it creates 3-dimensional cross-sectional images of the body while the X-ray instrument creates 2-dimensional images of the body; the 3-dimensional cross-sectional images are created by taking images from different angles, which is done by taking a series of tomographic images from different angles. The diverse images are collected by a computer and digitally stacked to form a 3-dimensional image of the patient. For creation of images by the CT instrument, a CT scanner uses a motorized X-ray source that rotates around the circular opening of a donut-shaped structure called a gantry while the X-ray tube rotates around the patient shooting narrow beams of X-rays through the body. Some of the applications where CT can be used can be blood clots; bone fractures, including subtle fractures not visible on X-ray; or organ injuries.

In some embodiments, the imaging system 136 includes ultrasound imaging, also referred to as sonography or ultrasonography, that uses ultrasound or sound waves (also referred to as acoustic waves) for the creation of cross-sectional images of the interior of the human body. Ultrasound waves in the imaging system 136 can be produced by a piezoelectric transducer, which produces sound waves and sends them into the body. The sound waves that are reflected are converted into electrical signals, which are sent to an ultrasound scanner. Ultrasound instruments can be used for diagnostic and functional imaging or for therapeutic or interventional procedures. Some of the applications where ultrasound can be used are diagnosis/treatment/guidance during medical procedures (e.g., biopsies, internal organs such as liver/kidneys/pancreas, fetal monitoring, etc.), in soft tissues, muscles, blood vessels, tendons, or joints. Ultrasound can be used for internal imaging (where the transducer is placed in organs, e.g., vagina) and external imaging (where the transducer is placed on the chest for heart monitoring or the abdomen for fetal monitoring). An ultrasound machine can consist of a monitor, keyboard, processor, data storage, probe, and transducer.

In some embodiments, the system 100 includes a stereotactic navigation system 138 that uses patient imaging (e.g., CT, MRI) to guide surgical robots in the placement of specialized surgical instruments and implants. The patient images are taken to guide a surgical robot before or during the medical procedure. The stereotactic navigation system 138 includes a camera having infrared sensors to determine the location of the tip of the probe being used in the surgical procedure. This information is sent in real-time so that the surgical robot has a clear image of the precise location where they are working in the body. The stereotactic navigation system 138 can be framed (requires attachment of a frame to the patient's head using screws or pins) or frameless (does not require the placement of a frame on the patient's anatomy). The stereotactic navigation system 138 can be used for diagnostic biopsies, tumor resection, bone preparation/implant placement, placement of electrodes, otolaryngologic procedures, or neurosurgical procedures.

In some embodiments, the system 100 includes an anesthesiology machine 140 that is used to generate and mix medical gases, such as oxygen or air, and anesthetic agents to induce and maintain anesthesia in patients. The anesthesiology machine 140 delivers oxygen and anesthetic gas to the patient and filters out expiratory carbon dioxide. The anesthesiology machine 140 can perform functions such as providing oxygen (O2), accurately mixing anesthetic gases and vapors, enabling patient ventilation, and minimizing anesthesia-related risks to patients and staff. The anesthesiology machine 140 can include the following essential components: a source of O2, O2 flowmeter, vaporizer (anesthetics include isoflurane, halothane, enflurane, desflurane, sevoflurane, and methoxyflurane), patient breathing circuit (tubing, connectors, and valves), and scavenging system (removes any excess anesthetics gases). The anesthesiology machine 140 can be divided into three parts: the high pressure system, the intermediate pressure system, and the low pressure system. The process of anesthesia starts with oxygen flow from a pipeline or cylinder through the flowmeter; the O2 flows through the vaporizer and picks up the anesthetic vapors; the O2-anesthetic mix then flows through the breathing circuit and into the patient's lungs, usually by spontaneous ventilation or normal respiration.

In some embodiments, the system 100 includes a surgical bed 142 equipped with mechanisms that can elevate or lower the entire bed platform; flex, or extend individual components of the platform; or raise or lower the head or the feet of the patient independently. The surgical bed 142 can be an operation bed, cardiac bed, amputation bed, or fracture bed. Some essential components of the surgical bed 142 can be a bed sheet, woolen blanket, bath towel, and bed block. The surgical bed 142 can also be referred to as a post-operative bed, which refers to a special type of bed made for the patient who is coming from the operation theater or from another procedure that requires anesthesia. The surgical bed 142 is designed in a manner that makes it easier to transfer an unconscious or weak patient from a stretcher/wheelchair to the bed. The surgical bed 142 should protect bed linen from vomiting, bleeding, drainage, and discharge; provide warmth and comfort to the patient to prevent shock; provide necessary positions, which are suitable for operation; protect patient from being chilled; and be prepared to meet any emergency.

In some embodiments, the system 100 includes a Jackson frame 144 (or Jackson table), which refers to a frame or table that is designed for use in spinal surgeries and can be used in a variety of spinal procedures in supine, prone, or lateral positions in a safe manner. Two peculiar features of the Jackson table 144 are the absence of central table support and an ability to rotate the table through 180 degrees. The Jackson table 144 is supported at both ends, which keeps the whole of the table free. This allows the visualization of a patient's trunk and major parts of extremities as well. The Jackson frame 144 allows the patient to be slid from the cart onto the table in the supine position with appropriate padding placed. The patient is then strapped securely on the Jackson table 144.

In some embodiments, the system 100 includes a disposable air warmer 146 (sometimes referred to as a Bair™ or Bair Hugger™). The disposable air warmer 146 is a convective temperature management system used in a hospital or surgery center to maintain a patient's core body temperature. The disposable air warmer 146 includes a reusable warming unit and a single-use disposable warming blanket for use during surgery. It can also be used before and after surgery. The disposable air warmer 146 uses convective warming consisting of two components: a warming unit and a disposable blanket. The disposable air warmer 146 filters air and then forces warm air through disposable blankets, which cover the patient. The blanket can be designed to use pressure points on the patient's body to prevent heat from reaching areas at risk for pressure sores or burns. The blanket can also include drainage holes where fluid passes through the surface of the blanket to linen underneath, which will reduce the risk of skin softening and reduce the risk of unintended cooling because of heat loss from evaporation.

In some embodiments, the system 100 includes a sequential compression device (SCD) 148 used to help prevent blood clots in the deep veins of legs. The sequential compression device 148 uses cuffs around the legs that fill with air and squeeze the legs. This increases blood flow through the veins of the legs and helps prevent blood clots. A deep vein thrombosis (DVT) is a blood clot that forms in a vein deep inside the body. Some of the risks of using the SCD 148 can be discomfort, warmth, sweating beneath the cuff, skin breakdown, nerve damage, or pressure injury.

In some embodiments, the system 100 includes a bed position controller 150, which refers to an instrument for controlling the position of the patient bed. Positioning a patient in bed is important for maintaining alignment and for preventing bedsores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient can be in the following positions in a bed: supine position, prone position, lateral position, Sims' position, Fowler's position, semi-Fowler's position, orthopedic or tripod position, or Trendelenburg position.

In some embodiments, the system 100 includes environmental controls 152. The environmental controls 152 can be operating room environmental controls for control or maintenance of the environment in the operating room 102 where procedures are performed to minimize the risk of airborne infection and to provide a conducive environment for everyone in the operating room 102 (e.g., surgeon, anesthesiologist, nurses, and patient). Some factors that can contribute to poor quality in the environment of the operating room 102 are temperature, ventilation, and humidity, and those conditions can lead to profound effects on the health and work productivity of people in the operating room 102. As an example: surgeons prefer a cool, dry climate since they work under bright, hot lights; anesthesia personnel prefer a warmer, less breezy climate; patient condition demands a relatively warm, humid, and quiet environment. The operating room environmental controls can control the environment by taking care of the following factors: environmental humidity, infection control, or odor control. Humidity control can be performed by controlling the temperature of anesthesia gases; infection can be controlled by the use of filters to purify the air.

In some embodiments, the environmental controls 152 include a heating, ventilation, and air conditioning (HVAC) system for regulating the environment of indoor settings by moving air between indoor and outdoor areas, along with heating and cooling. HVAC can use a different combination of systems, machines, and technologies to improve comfort. HVAC can be necessary to maintain the environment of the operating room 102. The operating room 102 can be a traditional operating room (which can have a large diffuser array directly above the operating table) or a hybrid operating room (which can have monitors and imaging equipment 136 that consume valuable ceiling space and complicate the design process). HVAC can include three main units, for example, a heating unit (e.g., furnace or boiler), a ventilation unit (natural or forced), and an air conditioning unit (which can remove existing heat). HVAC can be made of components such as air returns, filters, exhaust outlets, ducts, electrical elements, outdoor units, compressors, coils, and blowers. The HVAC system can use central heating and AC systems that use a single blower to circulate air via internal ducts.

In some embodiments, the environmental controls 152 include an air purification system for removing contaminants from the air in the operating room 102 to improve indoor air quality. Air purification can be important in the operating room 102 as surgical facility infection can be a reason for high mortality and morbidity. The air purification system can deliver clean, filtered, contaminant-free air over the surgical bed 142 using a diffuser, airflow, etc., to remove all infectious particles down and away from the patient. The air purification system can be an air curtain, multi-diffuser array, or single large diffuser (based on laminar diffuser flow) or High-Efficiency Particulate Air filter (HEPA filter). A HEPA filter protects a patient from infection and contamination using a filter, which is mounted at the terminal of the duct. A HEPA filter can be mounted on the ceiling and deliver clean, filtered air in a flow to the operating room 102 that provides a sweeping effect that pushes contaminants out via the return grilles that are usually mounted on the lower wall.

In some embodiments, the system 100 includes one or more medical or surgical tools 154. The surgical tools 154 can include orthopedic tools (also referred to as orthopedic instruments) used for treatment and prevention of deformities and injuries of the musculoskeletal system or skeleton, articulations, and locomotive system (i.e., set formed by skeleton, muscles attached to it, and the part of the nervous system that controls the muscles). A major percentage of orthopedic tools are made of plastic. The orthopedic tools can be divided into the following specialties: hand and wrist, foot and ankle, shoulder, and elbow, arthroscopic, hip, and knee. The orthopedic tools can be fixation tools, relieving tools, corrective tools, or compression-distraction tools. A fixation tool refers to a tool designed to restrict movements partially or completely in a joint, e.g., hinged splints (for preserving a certain range of movement in a joint) or rigid splints. A relieving tool refers to a tool designed to relieve pressure on an ailing part by transferring support to healthy parts of an extremity, e.g., Thomas splint and the Voskoboinikova apparatus. A corrective tool refers to a surgical tool designed to gradually correct a deformity, e.g., corsets, splints, orthopedic footwear, insoles, and other devices to correct abnormal positions of the foot. A compression-distraction tool refers to a surgical tool designed to correct acquired or congenital deformities of the extremities, e.g., curvature, shortening, and pseudarthrosis such as Gudushauri. A fixation tool can be an internal fixation tool (e.g., screws, plates) or external fixation tools used to correct a radius or tibia fracture. The orthopedic tools can be bone-holding forceps, drill bits, nail pins, hammers, staples, etc.

In some embodiments, the surgical tools 154 include a drill for making holes in bones for insertion of implants like nails, plates, screws, and wires. The drill tool functions by drilling cylindrical tunnels into bone. Drills can be used in orthopedics for performing medical procedures. If the drill does not stop immediately when used, the use of the drill on bones can have some risks, such as harm caused to bone, muscle, nerves, and venous tissues, which are wrapped by surrounding tissue. Drills vary widely in speed, power, and size. Drills can be powered as electrical, pneumatic, or battery. Drills generally can work on speeds below 1000 rpm in orthopedic settings. Temperature control of drills is an important aspect in the functioning of the drill and is dependent on parameters such as rotation speed, torque, orthotropic site, sharpness of the cutting edges, irrigation, and cooling systems. The drill can include a physical drill, power cord, electronically motorized bone drill, or rotating bone shearing incision work unit.

In some embodiments, the surgical tools 154 include a scalpel for slicing, cutting, or osteotomy of bone during orthopedic procedure. The scalpel can be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate but performs cutting by an ultrasonically oscillating or forward/backward moving metal tip. Scalpels can prevent injuries caused by a drill in a spinal surgery such as complications such as nerve thermal injury, grasping soft tissue, tearing dura mater, and mechanical injury.

In some embodiments, stitches (also referred to as sutures) or a sterile, surgical thread is used to repair cuts or lacerations and is used to close incisions or hold body tissues together after a surgery or an injury. Stitches can involve the use of a needle along with an attached thread. Stitches can be either absorbable (the stitches automatically break down harmlessly in the body over time without intervention) or non-absorbable (the stitches do not automatically break down over time and must be manually removed if not left indefinitely). Stitches can be based on material monofilament, multifilament, and barb. Stitches can be classified based on size. Stitches can be based on synthetic or natural material. Stitches can be coated or un-coated.

In some embodiments, the surgical tools 154 include a stapler used for fragment fixation when inter-fragmental screw fixation is not easy. When there is vast damage and a bone is broken into fragments, staples can be used between these fragments for internal fixation and bone reconstruction. For example, they can be used around joints in ankle and foot surgeries, in cases of soft tissue damage, or to attach tendons or ligaments to the bone for reconstruction surgery. Staplers can be made of surgical grade stainless steel or titanium, and they are thicker, stronger, and larger.

In some embodiments, other medical or surgical equipment, such as a set of articles, surgical tools, or objects, is used to implement or achieve an operation or activity. A medical equipment refers to an article, instrument, apparatus, or machine used for diagnosis, prevention, or treatment of a medical condition or disease, or to the detection, measurement, restoration, correction, or modification of structure/function of the body for some health purpose. The medical equipment can perform functions invasively or non-invasively. In some embodiments, the medical equipment includes components such as a sensor/transducer, a signal conditioner, a display, or a data storage unit, etc. In some embodiments, the medical equipment includes a sensor to receive a signal from instruments measuring a patient's body, a transducer for converting one form of energy to electrical energy, a signal conditioner such as an amplifier, filter, etc., to convert the output from the transducer into an electrical value, a display to provide a visual representation of the measured parameter or quantity, or a storage system to store data, which can be used for future reference. A medical equipment can perform diagnosis or provide therapy; for example, the equipment delivers air into the lungs of a patient who is physically unable to breathe, or breathes insufficiently, and moves it out of the lungs.

In some embodiments, the system includes a machine 156 to aid in breathing. The machine 156 can be a ventilator (also referred to as a respirator) that provides a patient with oxygen when they are unable to breathe on their own. A ventilator is required when a person is not able to breathe on their own. A ventilator can perform a function of gently pushing air into the lungs and allow it to come back out. The ventilator functions by delivery of positive pressure to force air into the lungs, while usual breathing uses negative pressure by the opening of the mouth, and air flows in. The ventilator can be required during surgery or after surgery. The ventilator can be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator can be used with a face mask (non-invasive ventilation, where the ventilation is required for a shorter duration of time) or with a breathing tube also referred to as an endotracheal tube (invasive ventilation, where the ventilation is required for a longer duration of time). Ventilator use can have some risks such as infections, fluid build-up, muscle weakness, lung damage, etc. The ventilator can be operated in various modes, such as assist-control ventilation (ACV), synchronized intermittent-mandatory ventilation (SIMV), pressure-controlled ventilation (PCV), pressure support ventilation (PSV), pressure-controlled inverse ratio ventilation (PCIRV), airway pressure release ventilation (APRV), etc. The ventilator can include a gas delivery system, power source, control system, safety feature, gas filter, and monitor.

In some embodiments, the machine 156 is a continuous positive airway pressure (CPAP) used for the treatment of sleep apnea disorder in a patient. Sleep apnea refers to a disorder in which breathing repeatedly stops and starts while a patient is sleeping, often because throat/airways briefly collapse or something temporarily blocks them. Sleep apnea can lead to serious health problems, such as high blood pressure and heart trouble. A CPAP instrument helps the patient with sleep apnea to breathe more easily during sleep by sending a steady flow of oxygen into the nose and mouth during sleep, which keeps the airways open and helps the patient to breathe normally. The CPAP machine can work by a compressor/motor, which generates a continuous stream of pressurized air that travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs oxygen. This helps the patient to not wake up to resume breathing. CPAP can have a nasal pillow mask, nasal mask, or full mask. CPAP instrument can include a motor, a cushioned mask, a tube that connects the motor to the mask, a headgear frame, and adjustable straps. The essential components can be a motor, a cushioned mask, and a tube that connects the motor to the mask.

In some embodiments, the system 100 includes surgical supplies, consumables 158, or necessary supplies for the system 100 to provide care within the hospital or surgical environment. The consumables 158 can include gloves, gowns, masks, syringes, needles, sutures, staples, tubing, catheters, or adhesives for wound dressing, in addition to other surgical tools needed by surgical robots, doctors, and nurses to provide care. Depending on the device, mechanical testing can be carried out in tensile, compression, or flexure; in dynamic or fatigue; via impact; or with the application of torsion. The consumables 158 can be disposable (e.g., time-saving, have no risk of healthcare-associated infections, and cost-efficient) or sterilizable (to avoid cross-contamination or risk of surgical site infections).

In some embodiments, the system 100 includes a robotic surgical system 160 (sometimes referred to as a medical robotic system or a robotic system) that provides intelligent services and information to the operating room 102 and the console 108 by interacting with the environment, including human beings, via the use of various sensors, actuators, and human interfaces. The robotic surgical system 160 can be employed for automating processes in a wide range of applications, ranging from industrial (manufacturing), domestic, medical, service, military, entertainment, space, etc. The medical robotic system market is segmented by product type into surgical robotic systems, rehabilitative robotic systems, non-invasive radiosurgery robots, and hospital and pharmacy robotic systems. Robotic surgeries can be performed using tele-manipulators (e.g., input devices 166 at the console 108), which use the surgeon's actions on one side to control one or more "effectors" on the other side. The medical robotic system 160 provides precision and can be used for remotely controlled, minimally invasive procedures. The robotic surgical system 160 includes computer-controlled electromechanical devices that work in response to controls (e.g., input devices 166 at the console 108) manipulated by the surgeons.

In some embodiments, the system 100 includes equipment tracking systems 162, such as RFID, which is used to tag an instrument with an electronic tag and tracks it using the tag. Typically, this could involve a centralized platform that provides details such as location, owner, contract, and maintenance history for all equipment in real-time. A variety of techniques can be used to track physical assets, including RFID, global positioning system (GPS), Bluetooth low energy (BLE), barcodes, near-field communication (NFC), Wi-Fi, etc. The equipment tracking system 162 includes hardware components, such as RFID tags, GPS trackers, barcodes, and QR codes. The hardware component is placed on the asset, and it communicates with the software (directly or via a scanner), providing the software with data about the asset's location and properties. In some embodiments, the equipment tracking system 162 uses electromagnetic fields to transmit data from an RFID tag to a reader. Reading of RFID tags can be done by portable or mounted RFID readers. The read range for RFID varies with the frequency used. Managing and locating important assets is a key challenge for tracking medical equipment. Time spent searching for critical equipment can lead to expensive delays or downtime, missed deadlines and customer commitments, and wasted labor. The problem has previously been solved by using barcode labels or manual serial numbers and spreadsheets; however, these require manual labor. The RFID tag can be passive (smaller and less expensive, read ranges are shorter, have no power of their own, and are powered by the radio frequency energy transmitted from RFID readers/antennas) or active (larger and more expensive, read ranges are longer, have a built-in power source and transmitter of their own).

In some embodiments, the system 100 includes medical equipment, computers, software, etc., located in the doctor's office 110 that is communicably coupled to the operating room 102 over the network 104. For example, the medical equipment in the doctor's office 110 can include a microscope 116 used for viewing samples and objects that cannot be seen with an unaided eye. The microscope 116 can have components such as eyepieces, objective lenses, adjustment knobs, a stage, an illuminator, a condenser, or a diaphragm. The microscope 116 works by manipulating how light enters the eye using a convex lens, where both sides of the lens are curved outwards. When light reflects off of an object being viewed under the microscope 116 and passes through the lens, it bends toward the eye. This makes the object look bigger than it is. The microscope 116 can be compound (light-illuminated and the image seen with the microscope 116 is two-dimensional), dissection or stereoscope (light-illuminated and the image seen with the microscope 116 is three-dimensional), confocal (laser-illuminated and the image seen with the microscope 116 is on a digital computer screen), scanning electron (SEM) (electron-illuminated and the image seen with the microscope 116 is in black and white), or transmission electron microscope (TEM) (electron-illuminated and the image seen with the microscope 116 is the high magnification and high resolution).

The system 100 includes an electronic health records (EHR) database 106 that contains patient records. The EHR are a digital version of patients' paper charts. The EHR database 106 can contain more information than a traditional patient chart, including, but not limited to, a patients' medical history, diagnoses, medications, treatment plans, allergies, diagnostic imaging, lab results, etc. In some embodiments, the steps for each procedure disclosed herein are stored in the EHR database 106. Electronic health records can also include data collected from the monitors 112 from historical procedures. The EHR database 106 is implemented using components of the example computer system 300 illustrated and described in more detail with reference to FIG. 3.

In some embodiments, the EHR database 106 includes a digital record of patients' health information, collected, and stored systematically over time. The EHR database 106 can include demographics, medical history, history of present illness (HPI), progress notes, problems, medications, vital signs, immunizations, laboratory data, or radiology reports. Software (in memory 164) operating on the console 108 or implemented on the example computer system 300 (e.g., the instructions 304, 308 illustrated and described in more detail with reference to FIG. 3) are used to capture, store, and share patient data in a structured way. The EHR database 106 can be created and managed by authorized providers and can make health information accessible to authorized providers across practices and health organizations, such as laboratories, specialists, medical imaging facilities, pharmacies, emergency facilities, etc. The timely availability of EHR data enables healthcare providers to make more accurate decisions and provide better care to the patients by effective diagnosis and reduced medical errors. Besides providing opportunities to enhance patient care, the EHR database 106 can also be used to facilitate clinical research by combining patients' demographics into a large pool. For example, the EHR database 106 can support a wide range of epidemiological research on the natural history of disease, drug utilization, and safety, as well as health services research.

The console 108 is a computer device, such as a server, computer, tablet, smartphone, smart speaker (e.g., the speaker 632 of FIG. 6), etc., implemented using components of the example computer system 300 illustrated and described in more detail with reference to FIG. 3. In some embodiments, the steps for each procedure disclosed herein are stored in memory 164 on the console 108 for execution.

In some embodiments, the operating room 102 or the console 108 includes high-definition monitors 124, which refer to displays in which a clearer picture is possible than with low-definition, low-resolution screens. The high-definition monitors 124 have a higher density of pixels per inch than past standard TV screens. Resolution for the high-definition monitors 124 can be 1280×720 pixels or more (e.g., Full HD, 1920×1080; Quad HD, 2560×1440; 4K, 3840×2160; 8K, 7680×4320 pixels). The high-definition monitor 124 can operate in progressive or interlaced scanning mode. High-definition monitors used in medical applications can offer improved visibility; allow for precise and safe surgery with rich color reproduction; provide suitable colors for each clinical discipline; provide better visibility, operability with a large screen and electronic zoom, higher image quality in low light conditions, better visualization of blood vessels and lesions, and high contrast at high spatial frequencies; be twice as sensitive as conventional sensors; and make it easier to determine tissue boundaries (fat, nerves, vessels, etc.).

In some embodiments, the console 108 includes an input interface or one or more input devices 166. The input devices 166 can include a keyboard, a mouse, a joystick, any hand-held controller, or a hand-controlled manipulator, e.g., a tele-manipulator used to perform robotic surgery.

In some embodiments, the console 108, the equipment in the doctor's office 110, and the EHR database 106 are communicatively coupled to the equipment in the operating room 102 by a direct connection, such as ethernet, or wirelessly by the cloud over the network 104. The network 104 is the same as or similar to the network 314 illustrated and described in more detail with reference to FIG. 3. For example, the console 108 can communicate with the robotic surgical system 160 using the network adapter 312 illustrated and described in more detail with reference to FIG. 3.

Figure 2:
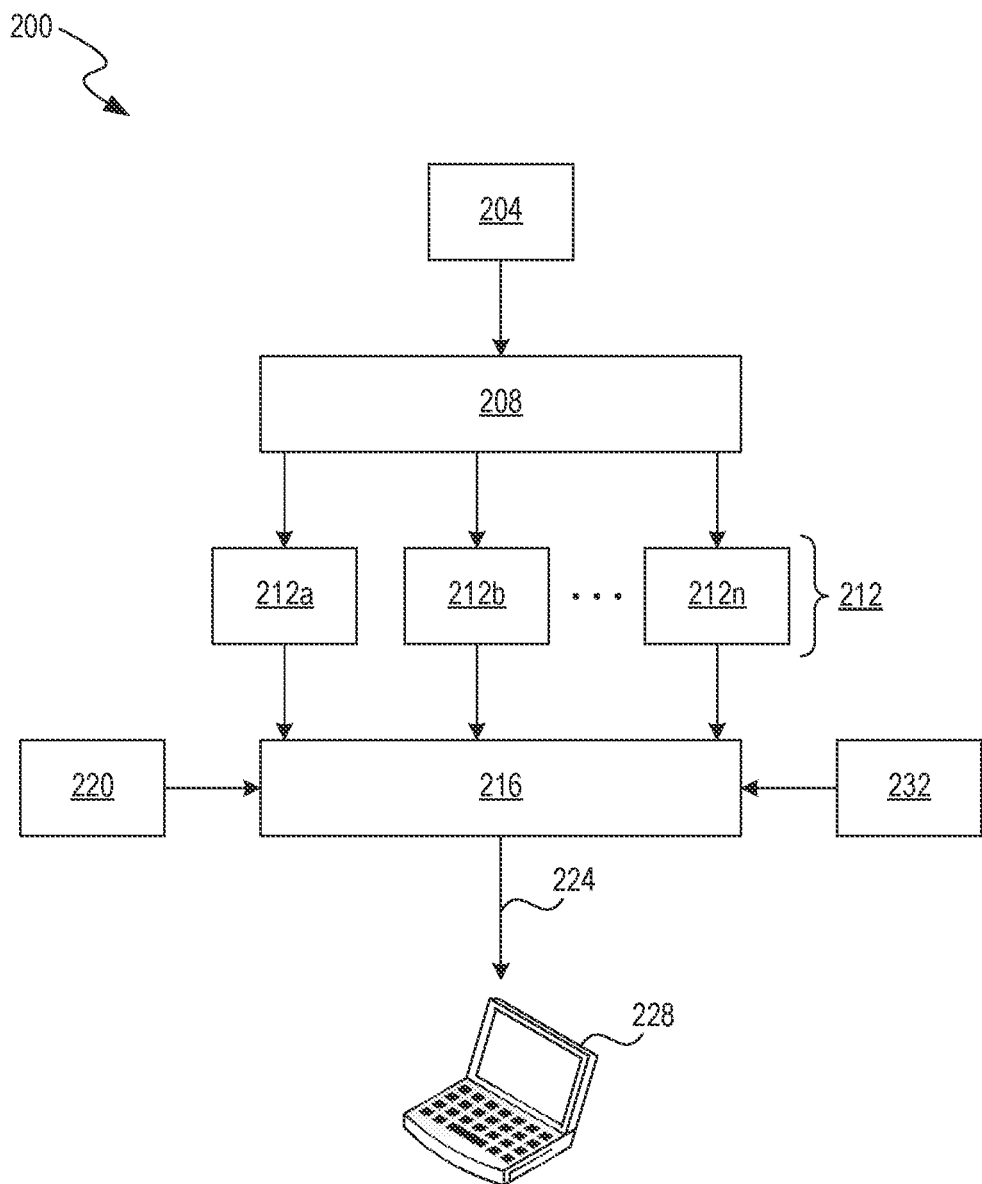
FIG. 2 is a block diagram illustrating an example machine learning (ML) system, in accordance with one or more embodiments.

FIG. 2 is a block diagram illustrating an example machine learning (ML) system 200, in accordance with one or more embodiments. The ML system 200 is implemented using components of the example computer system 300 illustrated and described in more detail with reference to FIG. 3. For example, the ML system 200 can be implemented on the console 108 using instructions programmed in the memory 164 illustrated and described in more detail with reference to FIG. 1. Likewise, embodiments of the ML system 200 can include different and/or additional components or be connected in different ways. The ML system 200 is sometimes referred to as a ML module.

The ML system 200 includes a feature extraction module 208 implemented using components of the example computer system 300 illustrated and described in more detail with reference to FIG. 3. In some embodiments, the feature extraction module 208 extracts a feature vector 212 from input data 204. For example, the input data 204 can include one or more physiological parameters measured by the monitors 112 illustrated and described in more detail with reference to FIG. 1. The feature vector 212 includes features 212a, 212b, . . . , 212n. The feature extraction module 208 reduces the redundancy in the input data 204, e.g., repetitive data values, to transform the input data 204 into the reduced set of features 212, e.g., features 212a, 212b, . . . , 212n. The feature vector 212 contains the relevant information from the input data 204, such that events or data value thresholds of interest can be identified by the ML model 216 by using this reduced representation. In some example embodiments, the following dimensionality reduction techniques are used by the feature extraction module 208: independent component analysis, Isomap, kernel principal component analysis (PCA), latent semantic analysis, partial least squares, PCA, multifactor dimensionality reduction, nonlinear dimensionality reduction, multilinear PCA, multilinear subspace learning, semidefinite embedding, autoencoder, and deep feature synthesis.

In alternate embodiments, the ML model 216 performs deep learning (also known as deep structured learning or hierarchical learning) directly on the input data 204 to learn data representations, as opposed to using task-specific algorithms. In deep learning, no explicit feature extraction is performed; the features 212 are implicitly extracted by the ML system 200. For example, the ML model 216 can use a cascade of multiple layers of nonlinear processing units for implicit feature extraction and transformation. Each successive layer uses the output from the previous layer as input. The ML model 216 can thus learn in supervised (e.g., classification) and/or unsupervised (e.g., pattern analysis) modes. The ML model 216 can learn multiple levels of representations that correspond to different levels of abstraction, wherein the different levels form a hierarchy of concepts. In this manner, the ML model 216 can be configured to differentiate features of interest from background features.

In alternative example embodiments, the ML model 216, e.g., in the form of a CNN generates the output 224, without the need for feature extraction, directly from the input data 204. The output 224 is provided to the computer device 228 or the console 108 illustrated and described in more detail with reference to FIG. 1. The computer device 228 is a server, computer, tablet, smartphone, smart speaker (e.g., the speaker 632 of FIG. 6), etc., implemented using components of the example computer system 300 illustrated and described in more detail with reference to FIG. 3. In some embodiments, the steps performed by the ML system 200 are stored in memory on the computer device 228 for execution. In other embodiments, the output 224 is displayed on the high-definition monitors 124 illustrated and described in more detail with reference to FIG. 1.

A CNN is a type of feed-forward artificial neural network in which the connectivity pattern between its neurons is inspired by the organization of a visual cortex. Individual cortical neurons respond to stimuli in a restricted region of space known as the receptive field. The receptive fields of different neurons partially overlap such that they tile the visual field. The response of an individual neuron to stimuli within its receptive field can be approximated mathematically by a convolution operation. CNNs are based on biological processes and are variations of multilayer perceptrons designed to use minimal amounts of preprocessing.

The ML model 216 can be a CNN that includes both convolutional layers and max pooling layers. The architecture of the ML model 216 can be "fully convolutional," which means that variable sized sensor data vectors can be fed into it. For all convolutional layers, the ML model 216 can specify a kernel size, a stride of the convolution, and an amount of zero padding applied to the input of that layer. For the pooling layers, the model 216 can specify the kernel size and stride of the pooling.

In some embodiments, the ML system 200 trains the ML model 216, based on the training data 220, to correlate the feature vector 212 to expected outputs in the training data 220. As part of the training of the ML model 216, the ML system 200 forms a training set of features and training labels by identifying a positive training set of features that have been determined to have a desired property in question, and, in some embodiments, forms a negative training set of features that lack the property in question.

The ML system 200 applies ML techniques to train the ML model 216, that when applied to the feature vector 212, outputs indications of whether the feature vector 212 has an associated desired property or properties, such as a probability that the feature vector 212 has a particular Boolean property, or an estimated value of a scalar property. The ML system 200 can further apply dimensionality reduction (e.g., via linear discriminant analysis (LDA), PCA, or the like) to reduce the amount of data in the feature vector 212 to a smaller, more representative set of data.

The ML system 200 can use supervised ML to train the ML model 216, with feature vectors of the positive training set and the negative training set serving as the inputs. In some embodiments, different ML techniques, such as linear support vector machine (linear SVM), boosting for other algorithms (e.g., AdaBoost), logistic regression, naïve Bayes, memory-based learning, random forests, bagged trees, decision trees, boosted trees, boosted stumps, neural networks, CNNs, etc., are used. In some example embodiments, a validation set 232 is formed of additional features, other than those in the training data 220, which have already been determined to have or to lack the property in question. The ML system 200 applies the trained ML model 216 to the features of the validation set 232 to quantify the accuracy of the ML model 216. Common metrics applied in accuracy measurement include: Precision and Recall, where Precision refers to a number of results the ML model 216 correctly predicted out of the total it predicted, and Recall is a number of results the ML model 216 correctly predicted out of the total number of features that had the desired property in question. In some embodiments, the ML system 200 iteratively re-trains the ML model 216 until the occurrence of a stopping condition, such as the accuracy measurement indication that the ML model 216 is sufficiently accurate, or a number of training rounds having taken place.

Figure 3:
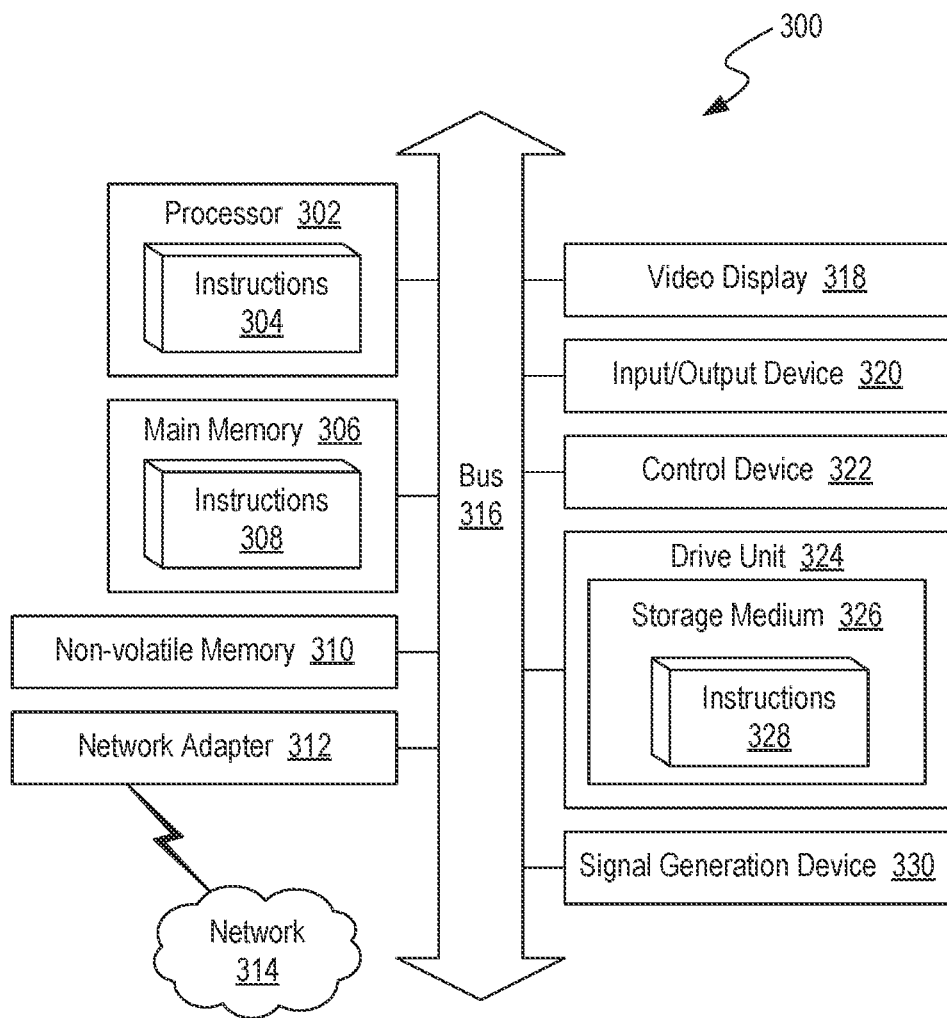
FIG. 3 is a block diagram illustrating an example computer system, in accordance with one or more embodiments.

FIG. 3 is a block diagram illustrating an example computer system, in accordance with one or more embodiments. Components of the example computer system 300 can be used to implement the monitors 112, the console 108, or the EHR database 106 illustrated and described in more detail with reference to FIG. 1. In some embodiments, components of the example computer system 300 are used to implement the ML system 200 illustrated and described in more detail with reference to FIG. 2. At least some operations described herein can be implemented on the computer system 300.

The computer system 300 can include one or more central processing units ("processors") 302, main memory 306, non-volatile memory 310, network adapters 312 (e.g., network interface), video displays 318, input/output devices 320, control devices 322 (e.g., keyboard and pointing devices), drive units 324 including a storage medium 326, and a signal generation device 320 that are communicatively connected to a bus 316. The bus 316 is illustrated as an abstraction that represents one or more physical buses and/or point-to-point connections that are connected by appropriate bridges, adapters, or controllers. The bus 316, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C)

bus, or an Institute of Electrical and Electronics Engineers (IEEE) standard 1394 bus (also referred to as "Firewire").

The computer system 300 can share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the computer system 300.

While the main memory 306, non-volatile memory 310, and storage medium 326 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 328. The term "machine-readable medium" and "storage medium" shall also be taken to include any medium that is capable of storing, encoding, or carrying a set of instructions for execution by the computer system 300.

In general, the routines executed to implement the embodiments of the disclosure can be implemented as part of an operating system or a specific application, component, program, object, module, or sequence of instructions (collectively referred to as "computer programs"). The computer programs typically include one or more instructions (e.g., instructions 304, 308, 328) set at various times in various memory and storage devices in a computer device. When read and executed by the one or more processors 302, the instruction(s) cause the computer system 300 to perform operations to execute elements involving the various aspects of the disclosure.

Moreover, while embodiments have been described in the context of fully functioning computer devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 310, floppy and other removable disks, hard disk drives, optical discs (e.g., Compact Disc Read-Only Memory (CD-ROMS), Digital Versatile Discs (DVDs)), and transmission-type media such as digital and analog communication links.

The network adapter 312 enables the computer system 300 to mediate data in a network 314 with an entity that is external to the computer system 300 through any communication protocol supported by the computer system 300 and the external entity. The network adapter 312 can include a network adapter card, a wireless network interface card, a router, an access point, a wireless router, a switch, a multilayer switch, a protocol converter, a gateway, a bridge, a bridge router, a hub, a digital media receiver, and/or a repeater.

The network adapter 312 can include a firewall that governs and/or manages permission to access proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall can additionally manage and/or have access to an access control list that details permissions including the access and operation rights of an object by an individual, a machine, and/or an application, and the circumstances under which the permission rights stand.

Figure 4A:
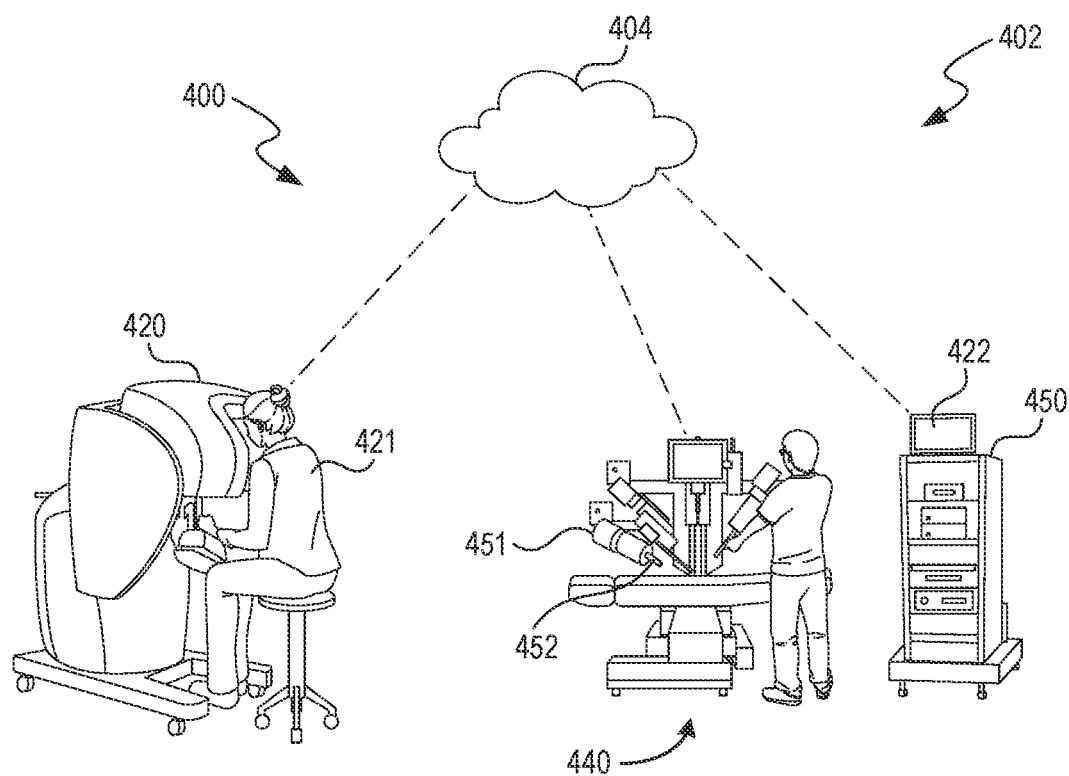
FIG. 4A is a block diagram illustrating an example robotic surgical system, in accordance with one or more embodiments.

FIG. 4A is a block diagram illustrating an example robotic surgical system 400, in accordance with one or more embodiments. The robotic surgical system 400 is the same as or similar to the robotic surgical system 160 illustrated and described in more detail with reference to FIG. 1. The robotic surgical system 400 can include components and features discussed in connection with FIGS. 1-3 and 4B-5. For example, the robotic surgical system 400 can include a console 420 with features of the console 108 of FIG. 1. Likewise, the components and features of FIG. 4A can be included or used with other embodiments disclosed herein. For example, the description of the input devices of FIG. 4A applies equally to other input devices (e.g., input devices 166 of FIG. 1).

The robotic surgical system 400 includes a user device or console 420 ("console 420"), a surgical robot 440, and a computer or data system 450. The console 420 can be operated by a surgeon and can communicate with components in an operating room 402, remote devices/servers, a network 404, or databases (e.g., database 106 of FIG. 1) via the network 404. The robotic surgical system 400 can include surgical control software and can include a guidance system (e.g., ML guidance system, AI guidance system, etc.), surgical planning software, event detection software, surgical tool software, etc. or other features disclosed herein to perform surgical step(s) or procedures or implement steps of processes discussed herein.

The user 421 can use the console 420 to view and control the surgical robot 440. The console 420 can be communicatively coupled to one or more components disclosed herein and can include input devices operated by one, two, or more users. The input devices can be hand-operated controls, but can alternatively, or in addition, include controls that can be operated by other parts of the user's body, such as, but not limited to, foot pedals. The console 420 can include a clutch pedal to allow the user 421 to disengage one or more sensor-actuator components from control by the surgical robot 440. The console 420 can also include display or output so that the one of more users can observe the patient being operated on, or the product being assembled, for example. In some embodiments, the display can show images, such as, but not limited to medical images, video, etc. For surgical applications, the images could include, but are not limited to, real-time optical images, real-time ultrasound, real-time OCT images and/or other modalities, or could include pre-operative images, such as MRI, CT, PET, etc. The various imaging modalities can be selectable, programmed, superimposed, and/or can include other information superimposed in graphical and/or numerical or symbolic form.

The robotic surgical system 400 can include multiple consoles 420 to allow multiple users to simultaneously or sequentially perform portions of a surgical procedure. The term "simultaneous" herein refers to actions performed at the same time or in the same surgical step. The number and configuration of consoles 420 can be selected based on the surgical procedure to be performed, number and configurations of surgical robots, surgical team capabilities, or the like.

Figure 4B:
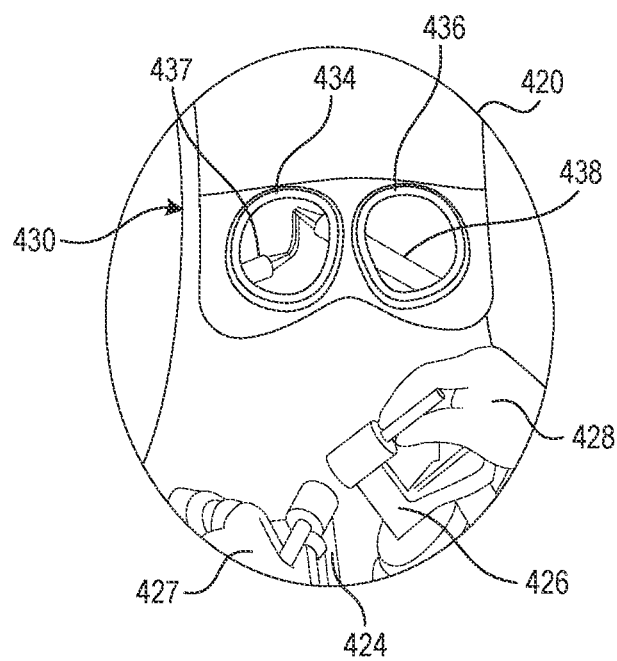
FIG. 4B illustrates an example console of the robotic surgical system of FIG. 4A, in accordance with one or more embodiments.

FIG. 4B illustrates an example console 420 of the robotic surgical system 400 of FIG. 4A, in accordance with one or more embodiments. The console 420 includes hand-operated input devices 424, 426, illustrated held by the user's left and right hands 427, 428, respectively. A viewer 430 includes left and right eye displays 434, 436. The user can view, for example, the surgical site, instruments 437, 438, or the like. The user's movements of the input devices 424, 426 can be translated in real-time to, for example, mimic the movement of the user on the viewer 430 and display (e.g., display 124 of FIG. 1) and within the patient's body while the user can be provided with output, such as alerts, notifications, and information. The information can include, without limitation, surgical or implantation plans, patient vitals, modification to surgical plans, values, scores, predictions, simulations, and other output, data, and information disclosed herein. The console 420 can be located at the surgical room or at a remote location.

The viewer 430 can display at least a portion of a surgical plan, including past and future surgical steps, patient monitor readings (e.g., vitals), surgical room information (e.g., available team members, available surgical equipment, surgical robot status, or the like), images (e.g., pre-operative images, images from simulations, real-time images, instructional images, etc.), and other surgical assist information. In some embodiments, the viewer 430 can be a VR/AR headset, display, or the like. The robotic surgical system 400, illustrated and described in more detail with reference to FIG. 4A, can further include multiple viewers 430 so that multiple members of a surgical team can view the surgical procedure. The number and configuration of the viewers 430 can be selected based on the configuration and number of surgical robots.

Referring again to FIG. 4A, the surgical robot 440 can include one or more controllers, computers, sensors, arms, articulators, joints, links, grippers, motors, actuators, imaging systems, effector interfaces, end effectors, or the like. For example, a surgical robot with a high number of degrees of freedom can be used to perform complicated procedures whereas a surgical robot with a low number of degrees of freedom can be used to perform simple procedures. The configuration (e.g., number of arms, articulators, degrees of freedom, etc.) and functionality of the surgical robot 440 can be selected based on the procedures to be performed.

The surgical robot 440 can operate in different modes selected by a user, set by the surgical plan, and/or selected by the robotic surgical system 400. In some procedures, the surgical robot 440 can remain in the same mode throughout a surgical procedure. In other procedures, the surgical robot 440 can be switched between modes any number of times. The configuration, functionality, number of modes, and type of modes can be selected based on the desired functionality and user control of the robotic surgical system 400. The robotic surgical system 400 can switch between modes based on one or more features, such as triggers, notifications, warnings, events, etc. Different example modes are discussed below. A trigger can be implemented in software to execute a jump to a particular instruction or step of a program. A trigger can be implemented in hardware, e.g., by applying a pulse to a trigger circuit.

In a user control mode, a user 421 controls, via the console 420, movement of the surgical robot 440. The user's movements of the input devices can be translated in real-time into movement of end effectors 452 (one identified).

In a semi-autonomous mode, the user 421 controls selected steps and the surgical robot 440 autonomously performs other steps. For example, the user 421 can control one robotic arm to perform one surgical step while the surgical robot 440 autonomously controls one or more of the other arms to concurrently perform another surgical step. In another example, the user 421 can perform steps suitable for physician control. After completion, the surgical robot 440 can perform steps involving coordination between three or more robotic arms, thereby enabling complicated procedures. For example, the surgical robot 440 can perform steps involving four or five surgical arms, each with one or more end effectors 452.

In an autonomous mode, the surgical robot 440 can autonomously perform steps under the control of the data system 450. The robotic surgical system 400 can be pre-programmed with instructions for performing the steps autonomously. For example, command instructions can be generated based on a surgical plan. The surgical robot 440 autonomously performs steps or the entire procedure. The user 421 and surgical team can observe the surgical procedure to modify or stop the procedure. Advantageously, complicated procedures can be autonomously performed without user intervention to enable the surgical team to focus and attend to other tasks. Although the robotic surgical system 400 can autonomously perform steps, the surgical team can provide information in real-time that is used to continue the surgical procedure. The information can include surgical robot input, surgical team observations, and other data input.

The robotic surgical system 400 can also adapt to the user control to facilitate completion of the surgical procedure. In some embodiments, the robotic surgical system 400 can monitor, via one or more sensors, at least a portion of the surgical procedure performed by the surgical robot 440. The robotic surgical system 400 can identify an event, such as a potential adverse surgical event, associated with a robotically performed surgical task. For example, a potential adverse surgical event can be determined based on acquired monitoring data and information for the end effector, such as surgical tool data from a medical device report, database, manufacturer, etc. The robotic surgical system 400 can perform one or more actions based on the identified event. The actions can include, without limitation, modification of the surgical plan to address the potential adverse surgical event, thereby reducing the risk of the event occurring. The adverse surgical event can include one or more operating parameters approaching respective critical thresholds, as discussed in connection with FIG. 12. The adverse surgical events can be identified using a machine learning model trained using, for example, prior patient data, training sets (e.g., tool data), etc.

In some embodiments, the robotic surgical system 400 determines whether a detected event (e.g., operational parameters outside a target range or exceeding a threshold, etc.) is potentially an adverse surgical event based on one or more criteria set by the robotic surgical system 400, user, or both. The adverse surgical event can be an adverse physiological event of the patient, surgical robotic malfunction, surgical errors, or other event that can adversely affect the patient or the outcome of the surgery. Surgical events can be defined and inputted by the user, surgical team, healthcare provider, manufacturer of the robotic surgery system, or the like.

The robotic surgical system 400 can take other actions in response to identification of an event. If the robotic surgical system 400 identifies an end effector malfunction or error, the robotic surgical system 400 can stop usage of the end effector and replace the malfunctioning component (e.g., surgical tool or equipment) to complete the procedure. The robotic surgical system 400 can monitor hospital inventory, available resources in the surgical room 402, time to acquire equipment (e.g., time to acquire replacement end effectors, surgical tools, or other equipment), and other information to determine how to proceed with surgery. The robotic surgical system 400 can generate multiple proposed surgical plans for continuing with the surgical procedure. The user and surgical team can review the proposed surgical plans to select an appropriate surgical plan. The robotic surgical system 400 can modify a surgical plan with one or more corrective surgical steps based on identified surgical complications, sensor readings, or the like. The surgical steps include, without limitation, cauterizing, cutting tissue, clamping tissue, stapling tissue, excising tissue, implanting items, alternative steps to replace planned surgical steps, manipulating tissue, or other steps disclosed herein. The surgical steps can be selected to keep the patient's vital(s) within a target range, for example, based on one or more surgical criteria (e.g., overall surgical time, length of surgical step, etc.).

The robotic surgical system 400 can retrieve surgical system information from a database to identify events. The database can describe, for example, maintenance of the robotic surgery system, specifications of the robotic surgery system, specifications of end effectors, surgical procedure information for surgical tools, consumable information associated with surgical tools, operational programs and parameters for surgical tools, monitoring protocols for surgical tools, or the like. The robotic surgical system 400 can use other information in databases disclosed herein to generate rules for triggering actions, identifying warnings, defining events, or the like. Databases can be updated with data (e.g., intraoperative data collected during the surgical procedure, simulation data, etc.) to intraoperatively adjust surgical plans, collect data for ML/AI training sets, or the like. Data from on-facility and off-facility simulations (e.g., pre-, or post-operative virtual simulations, simulations using models, etc.) can be generated and collected.

The surgical robot 440 can include robotic arms 451 (one identified) with robotic links, motors, and integrated or removable end effectors 452 (one identified). The end effectors 452 can include, without limitation, imagers (e.g., cameras, optical guides, etc.), robotic grippers, instrument holders, cutting instruments (e.g., cutters, scalpels, or the like), drills, cannulas, reamers, rongeurs, scissors, clamps, or other equipment or surgical tools disclosed herein. In some embodiments, the end effectors can be reusable or disposable surgical tools. The number and configuration of end effectors can be selected based on the configuration of the robotic system, procedure to be performed, surgical plan, etc. Imaging and viewing technologies can integrate with the surgical robot 440 to provide more intelligent and intuitive results.

The data system 450 can improve surgical planning, monitoring (e.g., via the display 422), data collection, surgical robotics/navigation systems, intelligence for selecting instruments, implants, etc. The data system 450 can execute, for example, surgical control instructions or programs for a guidance system (e.g., ML guidance system, AI guidance system, etc.), surgical planning programs, event detection programs, surgical tool programs, etc. For example, the data system 450 can increase procedure efficiency and reduce surgery duration by providing information insertion paths, surgical steps, or the like. The data system 450 can be incorporated into or include other components and systems disclosed herein.

The robotic surgical system 400 can be used to perform open procedures, minimally invasive procedures, such as laparoscopic surgeries, non-robotic laparoscopic/abdominal surgery, retroperitoneoscopy, arthroscopy, pelviscopy, nephroscopy, cystoscopy, cisternoscopy, sinoscopy, hysteroscopy, urethroscopy, and the like. The methods, components, apparatuses, and systems can be used with many different systems for conducting robotic or minimally invasive surgery. One example of a surgical system and surgical robots which can incorporate methods and technology is the DAVINCI™ system available from Intuitive Surgical, Inc.™ of Mountain View, California. However, other surgical systems, robots, and apparatuses can be used.

The robotic surgical system 400 can perform one or more simulations using selected entry port placements and/or robot positions, to allow a surgeon or other user to practice procedures. The practice session can be used to generate, modified, or select a surgical plan. In some embodiments, the system can generate a set of surgical plans for physician consideration. The physician can perform practice sessions for each surgical plan to determine and select a surgical plan to be implemented. In some embodiments, the systems disclosed herein can perform virtual surgeries to recommend a surgical plan. The physician can review the virtual simulations to accept or reject the recommended surgical plan. The physician can modify surgical plans pre-operative or intraoperatively.

Embodiments can provide a means for mapping the surgical path for neurosurgery procedures that minimize damage through artificial intelligence mapping. The software for artificial intelligence is trained to track the least destructive pathway. A surgical robot can make an initial incision based on a laser marking on the skin that illuminates the optimal site. Next, a robot can make a small hole and insert surgical equipment (e.g., guide wires, cannulas, etc.) that highlights the best pathway. This pathway minimizes the amount of tissue damage that occurs during surgery. Mapping can also be used to identify one or more insertion points associated with a surgical path. Mapping can be performed before treatment, during treatment, and/or after treatment. For example, pretreatment and posttreatment mapping can be compared by the surgeon and/or ML/AI system. The comparison can be used to determine next steps in a procedure and/or further train the ML/AI system.

Figure 5:
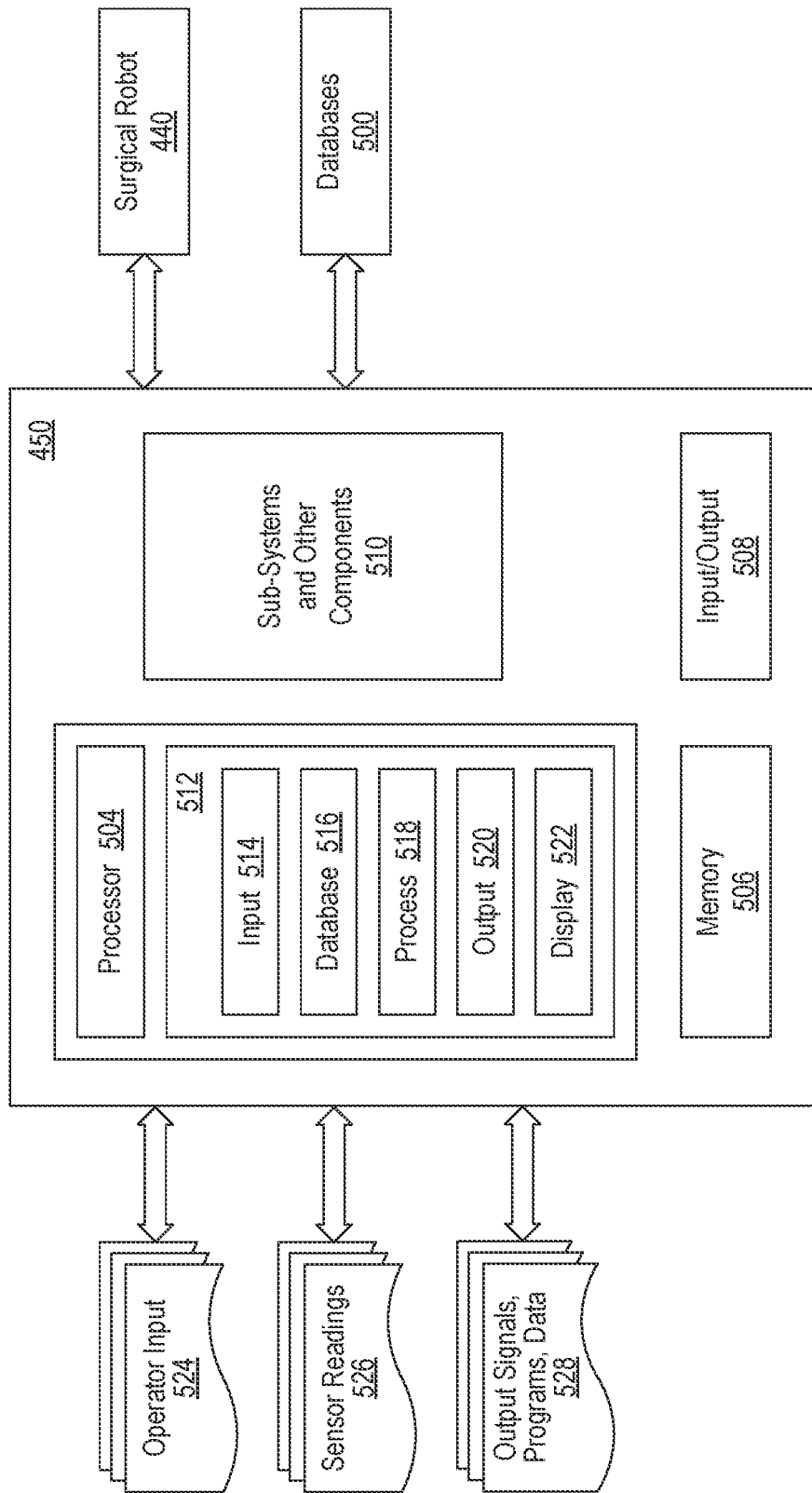
FIG. 5 is a schematic block diagram illustrating subcomponents of the robotic surgical system of FIG. 4A, in accordance with one or more embodiments.

FIG. 5 is a schematic block diagram illustrating subcomponents of the robotic surgical system 400 of FIG. 4A in accordance with embodiment of the present technology. The data system 450 has one or more processors 504, a memory 506, input/output devices 508, and/or subsystems and other components 510. The processor 504 can perform any of a wide variety of computing processing, image processing, robotic system control, plan generation or modification, and/or other functions. Components of the data system 450 can be housed in a single unit (e.g., within a hospital or surgical room) or distributed over multiple, interconnected units (e.g., though a communications network). The components of the data system 450 can accordingly include local and/or devices.

As illustrated in FIG. 5, the processor 504 can include a plurality of functional modules 512, such as software modules, for execution by the processor 504. The various implementations of source code (i.e., in a conventional programming language) can be stored on a computer-readable storage medium or can be embodied on a transmission medium in a carrier wave. The modules 512 of the processor 504 can include an input module 514, a database module 516, a process module 518, an output module 520, and, optionally, a display module 524 for controlling the display.

In operation, the input module 514 accepts an operator input 524 via the one or more input devices, and communicates the accepted information or selections to other components for further processing. The database module 516 organizes plans (e.g., robotic control plans, surgical plans, etc.), records (e.g., maintenance records, patient records, historical treatment data, etc.), surgical equipment data (e.g., instrument specifications), control programs, and operating records and other operator activities, and facilitates storing and retrieving of these records to and from a data storage device (e.g., internal memory 506, external databases, etc.). Any type of database organization can be utilized, including a flat file system, hierarchical database, relational database, distributed database, etc.

In the illustrated example, the process module 518 can generate control variables based on sensor readings 526 from sensors (e.g., end effector sensors of the surgical robot 440, patient monitoring equipment, etc.), operator input 524 (e.g., input from the surgeon console 420 and/or other data sources), and the output module 520 can communicate operator input to external computing devices and control variables to controllers. The display module 522 can be configured to convert and transmit processing parameters, sensor readings 526, output signals 528, input data, treatment profiles and prescribed operational parameters through one or more connected display devices, such as a display screen, touchscreen, printer, speaker system, etc.

In various embodiments, the processor 504 can be a standard central processing unit or a secure processor. Secure processors can be special-purpose processors (e.g., reduced instruction set processor) that can withstand sophisticated attacks that attempt to extract data or programming logic. The secure processors cannot have debugging pins that enable an external debugger to monitor the secure processor's execution or registers. In other embodiments, the system can employ a secure field-programmable gate array, a smartcard, or other secure devices.

The memory 506 can be standard memory, secure memory, or a combination of both memory types. By employing a secure processor and/or secure memory, the system can ensure that data and instructions are both highly secure and sensitive operations such as decryption are shielded from observation. In various embodiments, the memory 506 can be flash memory, secure serial EEPROM, secure field-programmable gate array, or secure application-specific integrated circuit. The memory 506 can store instructions for causing the surgical robot 440 to perform acts disclosed herein.

The input/output device 508 can include, without limitation, a touchscreen, a keyboard, a mouse, a stylus, a push button, a switch, a potentiometer, a scanner, an audio component such as a microphone, or any other device suitable for accepting user input and can also include one or more video monitors, a medium reader, an audio device such as a speaker, any combination thereof, and any other device or devices suitable for providing user feedback. For example, if an applicator moves an undesirable amount during a treatment session, the input/output device 508 can alert the subject and/or operator via an audible alarm. The input/output device 508 can be a touch screen that functions as both an input device and an output device.

The data system 450 can output instructions to command the surgical robot 440 and communicate with one or more databases 2600. The surgical robot 440 or other components disclosed herein can communicate to send collected data (e.g., sensor readings, instrument data, surgical robot data, etc.) to the database 500. This information can be used to, for example, create new training data sets, generate plans, perform future simulations, post-operatively analyze surgical procedures, or the like. The data system 450 can be incorporated, used with, or otherwise interact with other databases, systems, and components disclosed herein. In some embodiments, the data system 450 can be incorporated into the surgical robot 440 or other systems disclosed herein. In some embodiments, the data system 450 can be located at a remote location and can communicate with a surgical robot via one or more networks. For example, the data system 450 can communicate with a hospital via a network, such as a wide area network, a cellular network, etc. One or more local networks at the hospital can establish communication channels between surgical equipment within the surgical room.

A surgical program or plan ("surgical plan") can include, without limitation, patient data (e.g., pre-operative images, medical history, physician notes, etc.), imaging programs, surgical steps, mode switching programs, criteria, goals, or the like. The imaging programs can include, without limitation, AR/VR programs, identification programs (e.g., fiducial identification programs, tissue identification programs, target tissue identification programs, etc.), image analysis programs, or the like. Surgical programs can define surgical procedures or a portion thereof. For example, surgical programs can include end effector information, positional information, surgical procedure protocols, safety settings, surgical robot information (e.g., specifications, usage history, maintenance records, performance ratings, etc.), order of surgical steps, acts for a surgical step, feedback (e.g., haptic feedback, audible feedback, etc.), or the like. The mode switching programs can be used to determine when to switch the mode of operation of the surgical robot 440. For example, mode switching programs can include threshold or configuration settings for determining when to switch the mode of operation of the surgical robot 440. Example criteria can include, without limitation, thresholds for identifying events, data for evaluating surgical steps, monitoring criteria, patient health criteria, physician preference, or the like. The goals can include intraoperative goals, post-operative goals (e.g., target outcomes, metrics, etc.), goal rankings, etc. Monitoring equipment or the surgical team can determine goal progress, whether a goal has been achieved, etc. If an intraoperative goal is not met, the surgical plan can be modified in real-time so that, for example, the post-operative goal is achieved. The post-operative goal can be redefined intraoperatively in response to events, such as surgical complications, unplanned changes to patient's vitals, etc.

The surgical plan can also include healthcare information, surgical team information, assignments for surgical team members, or the like. The healthcare information can include surgical room resources, hospital resources (e.g., blood banks, standby services, available specialists, etc.), local or remote consultant availability, insurance information, cost information (e.g., surgical room costs, surgical team costs, etc.).

The systems disclosed herein can generate pre-operative plans and simulation plans. Pre-operative plans can include scheduling of equipment, surgical room, staff, surgical teams, and resources for surgery. The systems can retrieve information from one or more databases to generate the pre-operative plan based on physician input, insurance information, regulatory information, reimbursements, patient medical history, patient data, or the like. Pre-operative plans can be used to generate surgical plans, cost estimates, scheduling of consultants and remote resources, or the like. For example, a surgical plan can be generated based on available resources scheduled by the pre-operative plans. If a resource becomes unavailable, the surgical plan can be adjusted for the change in resources. The healthcare provider can be alerted if additional resources are recommended. The systems disclosed herein can generate simulation plans for practicing surgical procedures. On approval, a surgeon can virtually simulate a procedure using a console or another simulation device. Plans (e.g., surgical plans, implantation plans, etc.) can be generated and modified based on the surgeon's performance and simulated outcome.

The systems disclosed herein can generate post-operative plans for evaluating surgical outcomes, developing physical therapy and/or rehab programs and plans, etc. The post-operative plans can be modified by the surgical team, primary care provider, and others based on the recovery of the patient. In some embodiments, systems generate pre-operative plans, surgical plans, and post-operative plans prior to beginning a surgical procedure. The system then modifies one or more or the plans as additional information is provided. For example, one or more steps of the methods discussed herein can generate data that is incorporated into the plan. ML data sets to be incorporated into the plan generate a wide range of variables to be considered when generating plans. Plans can be generated to optimize patient outcome, reduce or limit the risk of surgical complications, mitigate adverse events, manage costs for surgical procedures, reduce recovery time, or the like. The healthcare provider can modify how plans are generated over time to further optimize based on one or more criteria.

Figure 6:
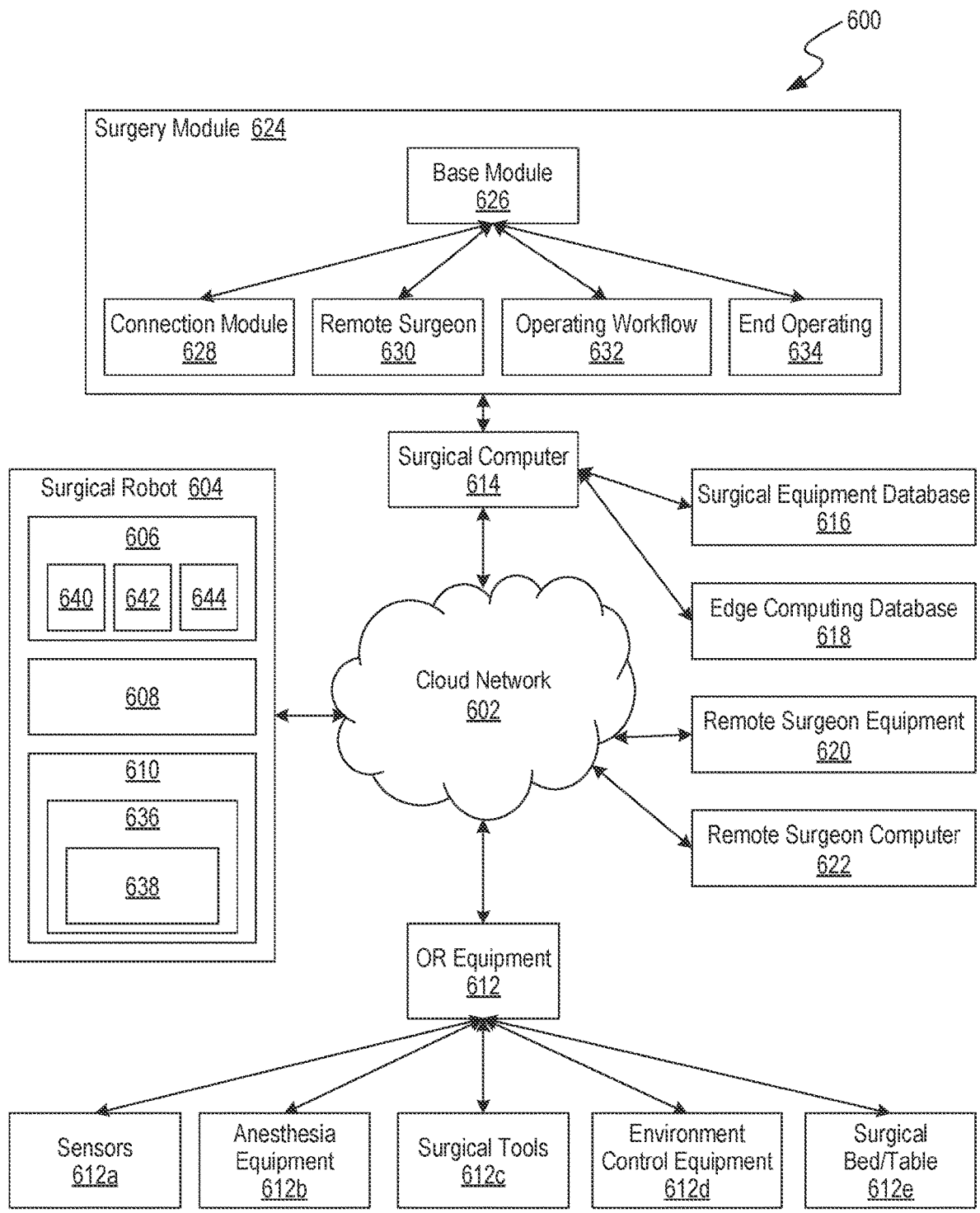
FIG. 6 is a block diagram illustrating an example robotic surgical system using edge computing and artificial intelligence (AI) for robotic telesurgery, in accordance with one or more embodiments.

FIG. 6 is a block diagram illustrating an example robotic surgical system 600 using edge computing and artificial intelligence (AI) for robotic telesurgery, in accordance with one or more embodiments. The system 600 includes a cloud network 602 and at least one surgical robot 604. A robotic "action" refers to one or more physical movements of a surgical robot (e.g., the surgical robot 440), such as aligning a surgical implant component or a surgical tool 154 (see FIG. 1), initiating the rotation of a rotary surgical tool, applying an axial force to a surgical tool, etc. The robotic surgical system 600 is implemented using the components of the example computer system 300 illustrated and described in more detail with reference to FIG. 3. Likewise, embodiments of the robotic surgical system 600 can include different and/or additional components or can be connected in different ways.

In embodiments, the surgical robot 604 is used for performing robotic telesurgery using edge computing. The surgical robot 604 includes multiple sensors 608. The sensors 608 are configured to measure at least a speed of the surgical robot 604 and capture images of a surgical site of the robotic telesurgery. The surgical site is in or on a body of a patient undergoing the surgery. The surgical robot 604 includes a robotic arm 606 that can be remotely controlled, multiple sensors 608, and an edge computing system 610. The surgical robot 604 is connected to the cloud network 602. Further, the system 600 includes operation room (OR) equipment 612. The OR equipment 612 can further include sensors 612a, anesthesia equipment 612b, one or more surgical tools 612c, environment control equipment 612d, and at least one surgical bed or table 612e.

In embodiments, the system 600 includes a surgical computer 614 connected to the cloud network 602. The surgical computer 614 can be coupled to a surgical equipment database 616 and an edge computing database 618. In embodiments, the surgical equipment database 616 and the edge computing database 618 are stored on the surgical robot 604 or communicably coupled to the surgical robot 604. The system 600 can include remote surgeon equipment 620 and a remote surgeon computer 622 to facilitate performance of the telesurgery procedure by the remote surgeon from a remote location. The surgical computer 614 can be coupled to a surgery module 624. The surgery module 624 includes a base module 626, a connection module 628, a remote surgeon module 630, an operating workflow module 632, and an end operating module 634. The modules are implemented using the components of the example computer system 300 illustrated and described in more detail with reference to FIG. 3. In embodiments, one or more of the surgery module 624, base module 626, connection module 628, remote surgeon module 630, operating workflow module 632, or the end operating module 634 are located on the surgical robot 604, e.g., operated by the AI accelerator 636.

The cloud network 602 is implemented using a collection of server devices to provide one or more services to the surgical robot 604 and a remote surgeon. The cloud network 602 can be coupled to the surgical robot 604, the OR equipment 612, or the surgical computer 614. The cloud network 602 can be a wired and/or a wireless network. The cloud network 602, if wireless, can be implemented using communication techniques such as Visible Light Communication (VLC), Worldwide Interoperability for Microwave Access (WiMAX), Long Term Evolution (LTE), Wireless Local Area Network (WLAN), Infrared (IR) communication, Public Switched Telephone Network (PSTN), radio waves, and other communication techniques known in the art. The cloud network 602 can allow ubiquitous access to shared pools of configurable resources and higher-level services that can be rapidly provisioned with minimal management effort, often over the Internet, and relies on sharing of resources to achieve coherence and economies of scale, like a public utility, while third-party clouds enable organizations to focus on their core businesses instead of expending resources on computer infrastructure and maintenance. Additionally, the cloud network 602 can be communicatively coupled to the surgical robot 604, the OR equipment 612, or the surgical computer 614, for real-time assistance in the OR. The cloud network 602 can also be synchronized with the surgical equipment database 616 and the edge computing database 618 to store information associated with the surgical robot 604 and the edge computing system 610 that corresponds to the telesurgery procedure in the OR.

In embodiments, the surgical robot 604 includes a robotic arm 606 that performs a surgical procedure. The robotic arm 606 is used to achieve desired surgical effects or perform specific actions during telesurgery, such as modifying a biological tissue or providing access for viewing the tissue. Remote controlled robotic arms 606 can facilitate performance of various telesurgery procedures from a remote surgeon computer 622. For example, the surgical robot can perform laparoscopic telesurgery, urologic telementoring, cholecystectomy, robotic gynecologic surgery, robotic prostate surgery, kidney surgery, colorectal surgery, single-site robotic gallbladder surgery, etc.

The robotic arm 606 is used for achieving desired effects or performing surgery. The robotic arm 606 is a mechanical arm, usually programmable, used to perform surgical procedures with more precision, flexibility, and control than is possible with conventional techniques. The robotic arm 606 can be the sum of the mechanisms or can be part of a more complex robot. For example, the robotic arm 606 can be implemented as a Cartesian robot, a collaborative robot, an anthropomorphic robot, a Selective Compliance Articulated Robot Arm (SCARA) robot, a spherical/polar robot, an articulated robot, or a parallel robot, without departing from the scope of the disclosure. In embodiments, the robotic arm 606 is manufactured by one of different manufacturers such as, but not limited to, Computer Motion Intuitive Surgical, Asensus Surgical, Embodied, SoftBank Robotics, Diligent Robotics, Barrett Technology, or Energid Technologies.

In embodiments, the robotic arm 606 is communicably coupled to the edge computing system 610. The robotic arm 606 includes one or more robotic links 640 and robotic joints 642 configured to move the robotic links to perform the robotic telesurgery. For example, the robotic arm 606 can be a serial robot arm having a chain of links moved by joints which are actuated by motors. In embodiments, the robotic arm 606 has a number of degrees of freedom corresponding to a number of the robotic joints 642. The number of degrees of freedom enable the robotic arm 606 to move to a spatial position and an orientation. For example, the robotic arms 606 can be classified according to the number of degrees of freedom. The number of degrees of freedom can equal the number of joints 642 that move the links 640 of the robotic arm 606. At least six degrees of freedom are required to enable the robotic arm 606 to reach an arbitrary pose (spatial position and orientation) in three-dimensional space. Additional degrees of freedom enable changes in the configuration of the links 640 in the robotic arm 606. The configuration of the robotic arm 606 can be determined using a mathematical process known as inverse kinematics, typically in terms of joint angles, given a desired pose of the robotic arm 606 in three-dimensional space. In embodiments, the surgical robot 604 is configured to position the robotic arm 606 in a first configuration to perform the robotic telesurgery. The first configuration is defined by a spatial position (e.g., a spatial position with respect to the patient, the surgical facility, or a robotic component) and an orientation (e.g., a horizontal orientation, a vertical orientation, an orientation with respect to a reference feature, such as a feature at the surgical facility, a reference frame, or a reference point). The robotic arm 606 is moved to a second configuration (and further configurations) based on instructions generated by the edge computing system 610.

The robotic arm 606 includes one or more end effectors 644 configured to perform at least one action to avoid the patient experiencing an adverse event when the robotic arm is positioned in a configuration. In embodiments, the surgical robot 604 performs the at least one action while obviating transfer of data to a remote computer over a network. The surgical robot 604 can determine whether to perform at least a portion of a surgical procedure on-the-edge or perform one or more edge computing processes based on whether a network connection is available, latency times of the cloud network 602, data speeds over the cloud network 602, stability of communication channels, or the like. If an adverse communication event (e.g., excess latency times, data speeds below a threshold, etc.) is identified, the surgical robot 604 can use edge computing to perform one or more surgical actions according to a surgical plan. In this manner, robotic telesurgery can be performed independent of adverse communication events. For example, the surgical robot 604 performs the action on the edge while avoiding or obviating concurrent data transfer between the surgical robot 604 and the surgical computer 614 over the cloud network 602. In embodiments, the surgical robot 604 uses edge computing to generate a prediction of an adverse surgical event and generate instructions for controlling the surgical robot 604 while obviating simultaneous transfer of data and control instructions between the surgical robot 604 and the surgery module 624 over the cloud network 602. In embodiments, the surgical robot 604 performs at least a portion of a surgical procedure while obviating concurrent communication with the remote surgeon computer 622 over the cloud network 602.

In embodiments, the end effector 644 is configured to perform an action using at least one of a drill, forceps, a scalpel, a retractor, a dilator, or a grasper. In embodiments, the end effector 644 is configured to perform an action using at least one of a surgical tool 612c, a gripping device, a probe, or an endoscope. For example, the end effector 644 can be, but is not limited to, a drill, forceps, a scalpel, a retractor, a dilator, or a grasper. Further, the end effector 644 can be a peripheral device that attaches to the robotic arm 606, allowing the robotic arm 606 to interact with the surgical site. In embodiments, the end effector 644 can be a surgical tool 154 (see FIG. 1), such as a gripping device, a probe, an endoscope, or a scalpel. The surgical tool 154 can be used for performing specific actions or achieving desired effects during a surgery, such as modifying biological tissue or providing access for viewing the tissue. A gripping device enables the robotic arm 606 to pick up and hold objects. In embodiments, a probe is implemented using a switch that triggers when making contact with a surface. A scalpel is a small and sharp-bladed instrument used to facilitate the surgery performed by the robotic arm 606. Examples of robotic arms are also discussed in connection with FIGS. 4A and 4B. The range of motion, degrees of freedom, and number of arms can be selected based on the procedures to be performed.

In embodiments, the sensors 608 are configured to measure at least one of a torque of the robotic arm 606, a temperature of the end effector 644, or a power status of the surgical robot 604. For example, the surgical robot 604 can include multiple sensors 608 for sensing information related to the surgical robot 604 being used in the telesurgery procedure in the OR (see FIG. 1). The multiple sensors 608 can be used to measure multiple parameters related to the movement and operation of the surgical robot 604 including, but not limited to, a speed of the surgical robot 604, a torque of the surgical robot 604, a temperature of the surgical robot 604, or a power status of the surgical robot 604. In embodiments, the one or more sensors 608 include at least one of a force sensor, a pressure sensor, a torque sensor, a temperature sensor, a power sensor, an accelerometer, a gyroscope, a speed sensor (e.g., a motor shaft sensor, a drive shaft sensor, etc.), a global positioning system (GPS) receiver, an imaging device, a camera (e.g., an infrared camera, a digital camera, a video camera, etc.), a wireless communication relay device, or a laser sensor. For example, the sensors 608 generally include state-of-the-art technology such as GPS, infrared cameras, wireless communication relay devices, or lasers to capture images, such as images of a surgical site, an end effector, a tool, or the like. The sensors 608 can transmit the sensed data to the edge computing system 610 for performing edge computing and providing instructions based on the sensed data.

In embodiments, the edge computing system 610 is communicably coupled to the sensors 608. The edge computing system 610 includes an artificial intelligence (AI) accelerator 636 configured to receive parameters measured by the sensors 608 and the images captured by the sensors 608. The edge computing system 610 operates on the data sensed by the sensors 608. The edge computing system 610 uses edge computing, which is a distributed computing paradigm that brings computation and data storage closer to the sources of data (sensors 608). The use of edge computing improves response times and reduces bandwidth usage. Edge computing is a topology- and location-sensitive form of distributed computing, while Internet of Things (IoT) is a use case instantiation of edge computing. Using the edge computing embodiments disclosed herein, rather than raw data being transmitted to a central data center (e.g., the surgical computer 614, the surgery module 624, the remote surgeon computer 622, etc.) for processing and analysis, the computation is instead performed where the data is actually generated. Only the results of the computing at the edge, such as surgical insights, equipment maintenance predictions, or other actionable answers, are sent to a remote server for review or other human interactions.

In embodiments, the robotic telesurgery system 600 is configured to perform actions while obviating transfer of data to a remote computer (e.g., surgery module 624, remote surgeon computer 622, etc.) over a network (e.g., cloud network 602). For example, the edge computing embodiments disclosed herein keep storage and processors (e.g., the AI accelerator 636) where the data is, often requiring little more than a partial rack of gear to operate on a LAN and process the data locally. In embodiments, the computing gear is deployed in shielded or hardened enclosures to protect the gear from extremes of temperature, moisture, and other environmental conditions. Further, processing often involves normalizing and analyzing the data stream to look for surgical insights, and only the results of the analysis are sent back to the principal data center. The healthcare industry has dramatically expanded the amount of patient data collected from sensors and other medical equipment. The embodiments exploit this data volume using edge computing to apply automation and machine learning to access the data, ignore "normal" data, and identify problem data so that the surgical robot 604 or remote surgeons can take immediate action to help patients avoid health incidents in real time.

In embodiments, the edge computing system 610 includes one or more machine learning (ML) models 638 operating on the AI accelerator 636. The ML models 638 are trained to generate a prediction of an adverse surgical event based on the measured parameters, the images, the outcomes from actions to avoid adverse events, etc. The training of the ML model 638 is described in more detail with reference to FIG. 2. The ML model 638 generates instructions for controlling the surgical robot 604 to avoid an adverse surgical event. For example, the edge computing system 610 can include high speed processors to compute data recommendations based on the data sensed by the sensors 608. The data recommendations can be based on, for example, operational speeds of the surgical robot 604, positional accuracies of the surgical robot 604 based on the operational speeds, detected calibrations of the surgical robot 604, and/or combinations thereof. Output from multiple sensors can be used to monitor operation of the surgical robot 604. For example, image data can be used to confirm accuracy of speed sensors of the surgical robot 604. The image data can also be used to move an end effector relative to an imaged surgical site, an anatomical feature, etc. For example, features of a surgical site can be identified using the image data. The movement, orientation, and/or positions of components of the surgical robot 604, tools, and/or other features can be determined in real-time using real-time images to generate additional instructions for the surgical robot 604. Image data can also be used to monitor actions to avoid the adverse surgical event, determine an adverse event has been avoided, etc.

In embodiments, the robotic telesurgery system 600 includes the edge computing system 610, which includes the artificial intelligence (AI) accelerator 636. The artificial intelligence (AI) accelerator 636 includes the machine learning (ML) model 638 trained to generate a prediction of an adverse surgical event based on images of a surgical site received from the one or more sensors 608. Further, the ML model 638 generates instructions for controlling the robotic telesurgery system 600 to avoid the adverse surgical event during the robotic telesurgery. Example methods for generating output from an ML model are illustrated and described in more detail with reference to FIG. 2. For example, the edge computing system 610 uses artificial intelligence (AI) and machine learning (ML) to provide instructions or recommendations based on correlations between data received from the sensors 608 of the surgical robot 604 and data received from the OR equipment 612. The ML models 638 analyze raw data from the sensors 608 and generate instructions for the telesurgery procedure being performed by the surgical robot 604.

In embodiments, the robotic telesurgery system 600 includes the one or more sensors 608 configured to measure at least one of a torque of the robotic arm 606, a temperature of the end effector 644, or a power status of the surgical robot 604. The AI/ML data can correspond to correlations between various types of data used to generate predictions of future events in telesurgery procedures. For example, an end effector used for the procedure is the Surgical Drill 2 (see FIG. 7) having a speed of 450 rotations per minute (rpm), a torque of 43.4±6.3 Newton millimeter (N mm), a temperature of 42.6 degrees Celsius, operating with a force of 2.2 N, and using images from a camera corresponding to the 8th thoracic vertebra (T8) of Alex's spinal cord. The temperature of the OR in Chicago is 24 degrees Celsius.

In embodiments, the robotic arm 606 is communicably coupled to the edge computing system 610 and includes robotic joints 642 configured to move the robotic arm 606 to perform the robotic telesurgery. The robotic telesurgery system 600 is configured to position the robotic arm 606 in a configuration based on the instructions. The configuration is defined by a spatial position and an orientation. The robotic telesurgery system 600 is configured to perform at least one action to avoid an adverse event when the robotic arm 606 is positioned in the configuration. For example, the AI/ML data processed by the edge computing system 610 corresponds to a predicted risk of the Surgical Drill 2 inserting a screw that touches the 9th thoracic vertebra (T9), causing pain to Alex. In embodiments, ML models are generated and trained on the surgical computer 614 or edge computing database 618 and executed on the edge computing system 610. The ML models are sent to the edge computing system 610. The edge computing system 610 tests data against the models, for providing instructions to the surgical robot 604, based on the data sensed by the surgical robot 604.

In embodiments, the robotic telesurgery system 600 includes one or more imaging devices or sensors 612*a*. The one or more imaging devices 612*a* include at least one of a magnetic resonance imaging (MRI) machine, an X-ray machine, or a camera. The imaging devices 612*a* are configured to capture images of the surgical site. For example, the OR equipment 612 includes the sensors 612*a*, which can include imaging devices such as, but not limited to, magnetic resonance imaging (MRI) machines, X-ray machines, or other imaging devices like a camera. Imaging devices can use strong magnetic fields and radio waves to produce detailed images of the inside of a patient's body or use radiation to create pictures inside of the patient's body. In addition, the sensors 612*a* can also include patient monitoring devices such as, but not limited to, electroencephalogram (EEG), which detects abnormalities in brain waves, or in the electrical activity of the brain, electrocardiography (ECG or EKG), oxygen saturation from a pulse oximeter (SpO2), blood pressure, and other patient monitoring devices.

In embodiments, the end effector 644 is configured to perform at least one action using at least one of a continuous-flow anesthesia machine, one or more surgical tools 612*c*, one or more environment controls 612*d*, or a motorized surgical bed 612*e*. For example, the anesthesia equipment 612*b* can include sedation devices or pharmaceuticals. The anesthesia equipment 612*b* is a continuous-flow anesthetic machine, which provides a steady flow of air containing a regulated supply of gas to deliver general anesthesia to patients as they undergo a medical procedure. For example, the anesthesia equipment 612*b* can be an oxygen mask or anesthetic vaporizers. Further, the anesthesia equipment 612*b* can differ in appearance, size, and degree of sophistication. The anesthesia equipment 612*b* can include sections for: ventilation, peripheral nerve stimulator, space for monitoring equipment, accessories, storage space, and a worktop.

In embodiments, the surgical tools 612*c* can include a surgical robot and handheld tools. Further, the surgical tools 612*c* can be connected to the cloud network 602. The surgical tools 612*c* are used to achieve desired effects or perform specific actions during surgery, such as modifying biological tissue or provide access for viewing the tissue. The surgical robot 604 can include robotic arms 606, links 640, joints 642, end effectors 644, and embedded control software. In embodiments, the control software provides autonomous or manual controls. Particular surgical tools 612*c* can include forceps, retractors, dilators, or graspers. The surgical tools 612*c* facilitate the performance of various surgical procedures by the surgical robot 604 or by the remote surgeon computer 622.

The environment controls 612*d* can include at least lighting, heating, ventilation, and air conditioning (HVAC) to control temperature of the environment, and audio associated with the OR. Surgical lighting can be a critical aspect in the OR for performing the telesurgery procedure. Further, the surgical light—also referred to as an operating light or surgical light-head—is a medical device intended to assist medical personnel during a surgical procedure by illuminating a local area or cavity of the patient. A combination of several surgical lights is often referred to as a "surgical light system." Further, the surgical lighting can be in compliance with standards as set by the International Electrotechnical Commission (IEC). For example, the standards for homogenous light state that the light should offer good illumination on a flat, narrow, or deep surface in a cavity, despite obstacles such as surgeons' heads or hands; the central illuminance should be between 160,000 and 40,000 lux; the D50 light field diameter should be at least 50% of the D10 light field diameter; and, for the purpose of distinguishing true tissue color in a cavity, the color rendering index (Ra) should be between 85 and 100. A goal is to provide thermal comfort and acceptable indoor air quality. HVAC is a sub-discipline of mechanical engineering, based on the principles of thermodynamics, fluid mechanics, and heat transfer. Further, refrigeration is sometimes added to the field's abbreviation, as HVAC&R or HVACR or "ventilation" is dropped, as in HACR. Further, HVAC is an important part of residential structures such as single family homes, apartment buildings, hotels and senior living facilities, medium to large industrial and office buildings such as skyscrapers and hospitals, where safe and healthy building conditions are regulated with respect to temperature and humidity, using fresh air from outdoors.

The surgical bed/table 612*e* can include information that relates to the surgical bed/table 612*e* present in the OR. In embodiments, the surgical bed/table 612*e*, sometimes called the operating room table, is the table on which the patient lies during the telesurgery procedure. This surgical equipment is usually found inside the OR. The surgical bed/table 612*e* can be made up of three components: an operating table column, the tabletop, and the transporter. Further, modern versions of the surgical bed/table 612*e* are available as both stationary and mobile units. There are a wide range of tabletops that can be used for both general surgery and for specialized disciplines. A mobile surgical bed/table 612*e*, however, tends to be equipped with a specific discipline in mind. The base, column, and tabletop form a unit. Unlike a mobile surgical bed/table 612*e* that is usually employed in hospitals with small operating departments, for example, in ambulant operating rooms, modern operating table systems are characterized by their great mobility. Further, special tabletops can be designed for a variety of surgical disciplines and, thanks to the ability to change these tops, they enable versatile use of an operating room. Further, the surgical bed/table 612*e* with a stationary column is more stable and more hygienic. The better transport options improve the patient flow from the patient transfer unit and the operating room considerably. Finally, the surgical bed/table 612*e* with stationary columns enables control elements to be integrated into image procedures, for example, angiography and computed tomography (CT).

FIG. 7 illustrates a structure of an example surgical equipment database 616 for edge computing for robotic telesurgery using artificial intelligence, in accordance with one or more embodiments. In embodiments, the system 600 includes the surgical computer 614, which handles the functioning of the system 600 during the telesurgery procedure. The surgical computer 614 can be in communication with the surgical equipment database 616 for storing data. The surgical equipment database 616 can be located on the surgical robot 604 or remote. The surgical equipment database 616 stores information related to the surgical robot 604. The surgical equipment database 616 is implemented using the components of the example computer system 300 illustrated and described in more detail with reference to FIG. 3. Likewise, embodiments of the surgical equipment database 616 can include different and/or additional components or can be connected in different ways.

In embodiments, the surgical equipment database 616 can include, but not be limited to, the type of the surgical equipment, speed of the surgical equipment, torque of the surgical equipment, or temperature of the surgical equipment. For example, the surgical equipment database 616 includes data corresponding to Surgical Drill 1 operating at a speed of 500 rotations per minute (rpm), with a torque of 67.2±8.4 Newton millimeter (N mm), with a temperature of 34.2 degrees Celsius, and a force of 2 Newton. Further, the surgical equipment database 616 includes data corresponding to Surgical Drill 2 operating at a speed of 450 rotations per minute (rpm), with a torque of 43.4±6.3 Newton millimeter (N mm), with a temperature of 42.6 degrees Celsius, and a force of 2.2 Newton. Further, the surgical equipment database 616 includes data corresponding to Surgical Drill 3, operating at a speed of 560 rotations per minute (rpm), with a torque of 82.7±3.7 Newton millimeter (N mm), with a temperature of 39.1 degrees Celsius, and a force of 2.5

Newton. Further, the surgical equipment database 616 includes data corresponding to a Spinal Surgery Robotic Arm Inserter-1 operating at a torque of 7.2±8 Newton millimeter (N mm), with a temperature of 31.9 degrees Celsius, and a force of 9.8 Newton. A spinal surgery robotic arm inserter (sometimes referred to as a "spinal inserter") is a device used to insert a spinal implant, a rod, a screw, etc., into a patient's spine. Further, the surgical equipment database 616 includes data corresponding to a Spinal Surgery Robotic Arm Inserter-2, operating at a torque of 8.34±2.7 Newton millimeter (N mm), with a temperature of 33.2 degrees Celsius, and a force of 10.4 Newton.

FIG. 8 illustrates a structure of an example edge computing database 618 for edge computing for robotic telesurgery using artificial intelligence, in accordance with one or more embodiments. In embodiments, the surgical computer 614 can be in communication with the edge computing database 618, for storing information related to the at least one surgical equipment 604, the EMG data from the at least one surgical equipment 604, the risks identified by the edge computing, and recommendations provided by a surgeon. The edge computing database 618 can be located on the surgical robot 604 or remote. The edge computing database 618 is implemented using the components of the example computer system 300 illustrated and described in more detail with reference to FIG. 3. Likewise, embodiments of the edge computing database 618 can include different and/or additional components or can be connected in different ways.

In an example, the Surgical Drill 1 operates using sensor data related to an image of Alex's spine at the 7th thoracic vertebra (T7) with a prediction generated that a screw to be inserted may touch the 8th thoracic vertebra (T8), causing pain to Alex. The edge computing system 610 generates instructions for inserting a shorter screw. In another example, the Surgical Drill 2 operates using sensor data related to an image of Alex's spine at the 8th thoracic vertebra (T8) with a generated prediction that a screw to be inserted may touch the 9th thoracic vertebra (T9), causing pain to Alex. The edge computing system 610 generates instructions for inserting a shorter screw. In another example, the Surgical Drill 3 operates using sensor data related to an image of Alex's spine at the 9th thoracic vertebra (T9) with a generated prediction that a screw to be inserted may touch the 8th thoracic vertebra (T8), causing pain to Alex. The edge computing system 610 generates instructions for inserting a shorter screw.

In another example, the Spinal Surgery Robotic Arm Inserter-1 receives sensor data related to an image of Alex's spine with a generated prediction that a rod to be inserted may be dislocated by 0.1 cm to the left of the desired location. The edge computing system 610 generates instructions for correction during insertion of the rod to recalibrate the robotic arm inserter. In another example, the Spinal Surgery Robotic Arm Inserter-2 receives sensor data related to an image of Alex's spine with a risk identified that a rod to be inserted may be dislocated by 0.2 cm to the left of the desired location. The remote surgeon computer 622 sends a recommendation for correction during insertion of the rod to recalibrate the robotic arm inserter. The robotic arm inserter can facilitate the work of a remote surgeon with force transducer data, without departing from the scope of the disclosure.

In embodiments, the surgical computer 614 is coupled to the remote surgeon equipment 620. The remote surgeon equipment 620 can include a user interface (UI) to allow a remote surgeon to view patient data. Further, the remote surgeon equipment 620 can allow the remote surgeon to view one or more data related to the patient from a medical database via the cloud network 602. Further, the remote surgeon equipment 620 can allow the remote surgeon to monitor a live feed from the OR. In addition, the remote surgeon equipment 620 can allow the remote surgeon to take any audio and/or video from the surgical facility or the OR.

Further, the surgical computer 614 can be coupled to a remote surgeon computer 622. The remote surgeon computer 622 can include a controller and communication hardware. Further, the controller can be used to process the control signals that the remote surgeon may receive during the telesurgery. In embodiments, the controller can be a digital signal controller (DSC) for processing the control signals received during the telesurgery. The DSC can be a hybrid of microcontrollers and digital signal processors (DSPs). In other embodiments, the controller can be a microcontroller to process the control signals received during the telesurgery.

The controller can be manufactured by different manufacturers such as Microchip, Freescale, and Texas Instruments. Further, the controller can also include haptics. Haptics are also known as kinesthetic communication or 3D touch, which refers to any technology that can create an experience of touch by applying forces, vibrations, or motions to the user. Further, haptics can be enabled by various haptic devices, which work on force feedback by means of which the remote surgeon gains information about resistance and sensation on some part of the body. Further, the communication hardware can be used to establish communication between the surgical facility and the remote surgeon, monitoring from a distance to take input from the operating room and send surgical control signals. The communication hardware can be used at the remote surgeon facility. In embodiments, the communication can include audio and/or visual support. Further, the communication hardware can also include a microphone, and network equipment at the remote surgeon facility.

In embodiments, the surgical computer 614 can be coupled to the surgery module 624. The surgery module 624 checks and maintains a connection between the surgical robot 604 and the OR equipment 612. Further, the surgery module 624 establishes a connection between the remote surgeon, the surgical robot 604 and the OR equipment 612. In addition, the surgery module 624 can determine a risk assessment related to the surgical tools 612c used for the telesurgery procedure and then communicate the risk to the surgical robot 604 to provide instructions for performing the telesurgery procedure efficiently.

Figure 9:
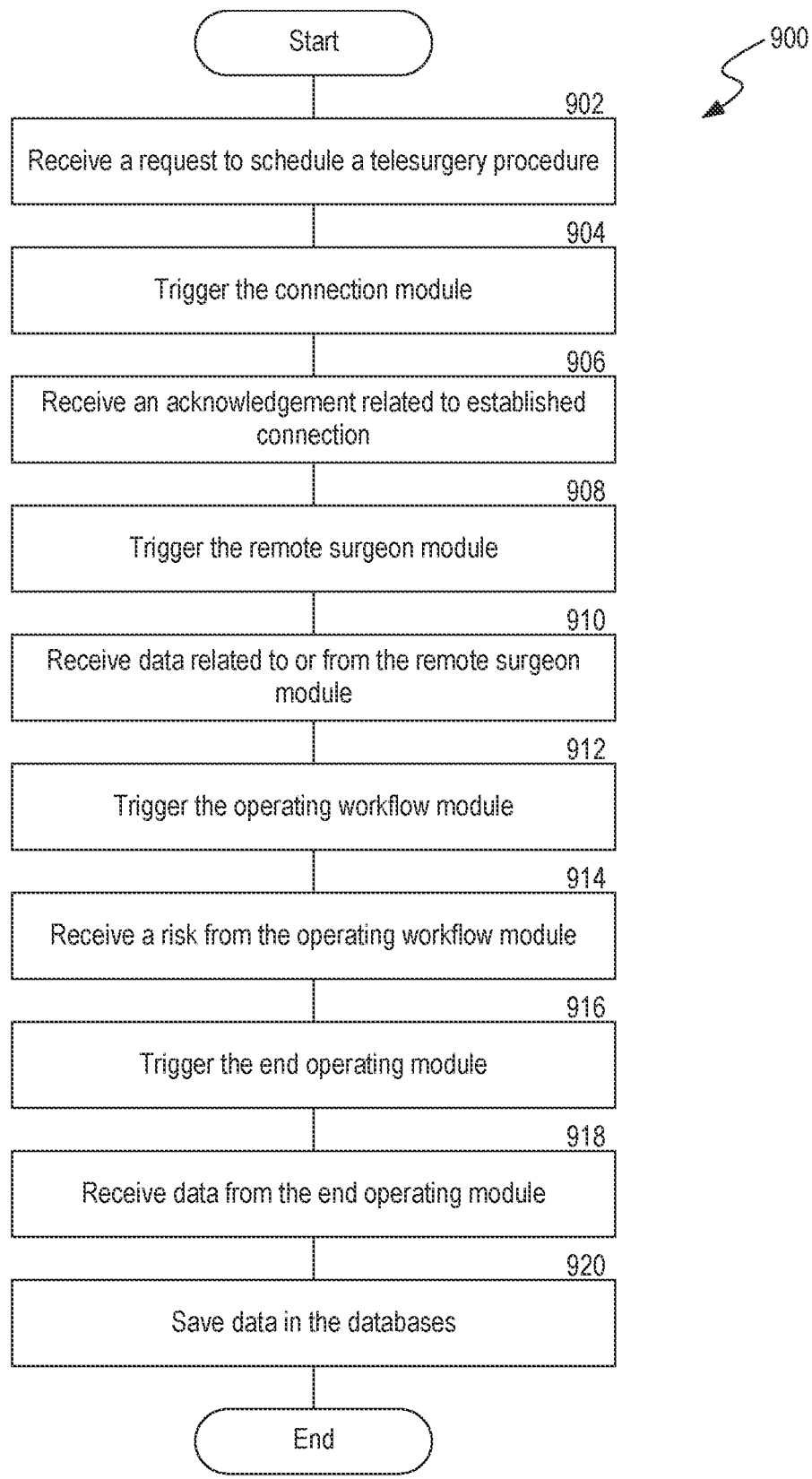
FIG. 9 is a flow diagram illustrating an example process for edge computing for robotic telesurgery using artificial intelligence, in accordance with one or more embodiments.

FIG. 9 is a flow diagram illustrating an example process 900 for edge computing for robotic telesurgery using artificial intelligence, in accordance with one or more embodiments. In some embodiments, the process 900 of FIG. 9 is performed by the base module 626. The base module 626 is illustrated and described in more detail with reference to FIG. 6. In other embodiments, the process 900 of FIG. 9 is performed by a computer system, e.g., the example computer system 300 illustrated and described in more detail with reference to FIG. 3. Particular entities, for example, the console 108 or the robotic surgical system 160 perform some or all of the steps of the process 900 in other embodiments. The console 108 and the robotic surgical system 160 are illustrated and described in more detail with reference to FIG. 1. Likewise, embodiments can include different and/or additional steps, or perform the steps in different orders.

The surgery module 624 includes the base module 626 for performing the operations disclosed in process 900 of FIG. 9. In some alternative implementations, the functions noted in process 900 can occur out of the order noted in FIG. 900. For example, two steps shown in succession in FIG. 9 can in fact be executed substantially concurrently or the steps can sometimes be executed in the reverse order, depending upon the functionality involved. In addition, the process descriptions or steps can represent decisions made by a hardware structure such as a state machine.

In step 902, the base module 626 receives a request from a surgical location to schedule a telesurgery procedure. For example, Alex is diagnosed with a fracture in his spine and is being operated on in a surgical facility in Chicago. The surgery is being performed via telesurgery overseen by Dr. T from a remote facility in San Francisco. The base module 626 receives a request from the surgical facility in Chicago to schedule the telesurgery procedure for Alex.

In step 904, the base module 626 triggers the connection module 628. The connection module 628 facilitates the establishment of a connection between the surgical robot 604 and the OR equipment 612. The connection can be established using the network adapter 312 and network 314 illustrated and described in more detail with reference to FIG. 3. In step 906, the base module 626 receives an acknowledgement related to the established connection. For example, the base module 626 receives an acknowledgement that the Surgical Drill 2 and a camera are successfully connected to the cloud network 602 for use in the telesurgery procedure to be performed on Alex.

In step 908, after receiving the acknowledgement, the base module 626 triggers the remote surgeon module 630. The remote surgeon module 630 can be triggered for establishing a connection between the remote surgeon and the equipment 612 available at the surgical facility, such as surgical drills or sensors. In step 910, the base module 626 receives data related to the OR from the remote surgeon module 630. For example, the base module 626 receives data from the camera and the Surgical Drill 2 with information related to the patient Alex and his spinal fracture. In step 912, the base module 626 triggers the operating workflow module 632.

In step 914, the base module 626, receives data corresponding to the risk assessment from the operating workflow module 632. For example, base module 626 receives data that there is a risk that the Surgical Drill 2 may insert the screw at the 8th thoracic vertebra (T8) of Alex's spinal cord to touch the 9th thoracic vertebra (T9), causing pain to Alex. In embodiments, the data corresponding to the risk is shared with the remote surgeon via the remote surgeon computer 622. In step 916, the base module 626 triggers the end operating module 634.

In step 918, the base module 626, receives data from the end operating module 634. In step 920, after receiving the data from the end operating module 634, the base module 626 saves the data in the surgical equipment database 616 and the edge computing database 618. For example, the base module 626 saves the data into the surgical equipment database 616 and the edge computing database 618. A remote surgeon can, e.g., override the force limitations for rod insertion based on the data received from the surgical robot 604, without departing from the scope of the disclosure.

Figure 10:
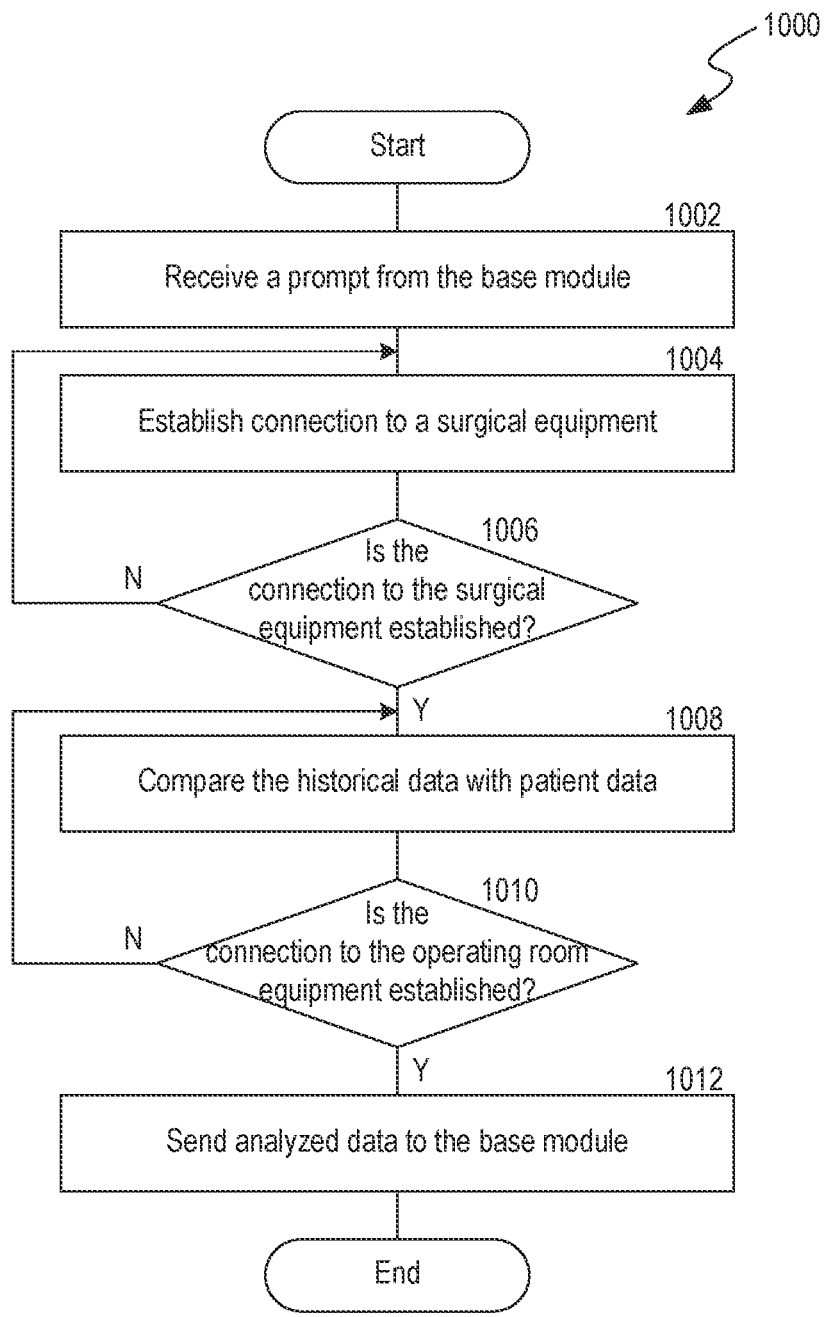
FIG. 10 is a flow diagram illustrating an example process for edge computing for robotic telesurgery using artificial intelligence, in accordance with one or more embodiments.

FIG. 10 is a flow diagram illustrating an example process 1000 for edge computing for robotic telesurgery using artificial intelligence, in accordance with one or more embodiments. In some embodiments, the process 1000 of FIG. 10 is performed by the connection module 628. The connection module 628 is illustrated and described in more detail with reference to FIG. 6. In other embodiments, the process 1000 of FIG. 10 is performed by a computer system, e.g., the example computer system 300 illustrated and described in more detail with reference to FIG. 3. Particular entities, for example, the console 108 or the robotic surgical system 160 perform some or all of the steps of the process 1000 in other embodiments. The console 108 and the robotic surgical system 160 are illustrated and described in more detail with reference to FIG. 1. Likewise, embodiments can include different and/or additional steps, or perform the steps in different orders.

In some alternative implementations, the functions noted in process 1000 occur out of the order noted in the drawings. For example, two steps shown in succession in FIG. 10 can in fact be executed substantially concurrently or the steps can sometimes be executed in the reverse order, depending upon the functionality involved. In addition, the process descriptions or steps in the flowchart can represent decisions made by a hardware structure such as a state machine.

In step 1002, the connection module 628 receives a prompt from the base module 626. The connection module 628 can establish a connection between the surgical robot 604 and the OR equipment 612. In step 1004, after receiving the prompt from the base module 626, the connection module 628 establishes a connection to the surgical robot 604. In embodiments, the connection module 628 establishes a connection from the surgical robot 604 to the cloud network 602 for the surgical robot 604 to be operational during the telesurgery procedure. For example, the connection module 628 establishes a connection between a Surgical Drill 1, a Surgical Drill 2, a Surgical Drill 3, a Spinal Surgery Robotic Rod Inserter-1, and a Spinal Surgery Robotic Rod Inserter-2, and the cloud network 602, for use during the telesurgery procedure to be performed on Alex.

In step 1006, the connection module 628 monitors whether the connection to the surgical robot 604 is established. In one case, if the connection to the surgical robot 604 is not established, the connection module 628 moves to step 1004 to establish the connection to the surgical robot 604. For example, if the Surgical Drill 2 is not functional, the connection module 628 again establishes the connection to the Surgical Drill 2. In another case, if the connection to the surgical robot 604 is established, then the connection module 628 moves to step 1008 to compare stored historical data with patient data. The historical data can include data gathered from previous surgeries.

In step 1008, the connection module 628 can also establish a connection to the OR equipment 612. In embodiments, the connection module 628 establishes a connection from the OR equipment 612 to the cloud network 602 for the OR equipment 612 to be operational during the telesurgery procedure. The OR equipment 612 includes the sensors 612a, the anesthesia equipment 612b, the one or more surgical tools 612c, the at least one environment control equipment 612d, and the at least one surgical bed or table 612e. For example, the connection module 628 establishes a connection between a camera, an HVAC equipment of the surgical facility in Chicago, and Surgical Bed 10 for Alex to the cloud network 602 for use during the telesurgery procedure to be performed on Alex.

In step 1010, the connection module 628 monitors whether the connection to the OR equipment 612 is established. In one case, if the connection to the OR equipment 612 is not established, the connection module 628 moves to step 1008 to again establish the connection to the one or more OR equipment 612. For example, if the camera is not functional, then the connection module 628 again establishes the connection to the camera. In another case, if the connection to the OR equipment 612 is established, then the connection module 628 moves to step 1012, to send analyzed data to the base module.

In step 1012, the connection module 628 sends an acknowledgement to the base module 626. The acknowledgement can include information related to a successful connection of the surgical robot 604 and the OR equipment 612. For example, the connection module 628 sends an acknowledgement that the Surgical Drill 2 and the camera are successfully connected to the cloud network 602, for use during the telesurgery procedure to be performed on Alex.

Figure 11:
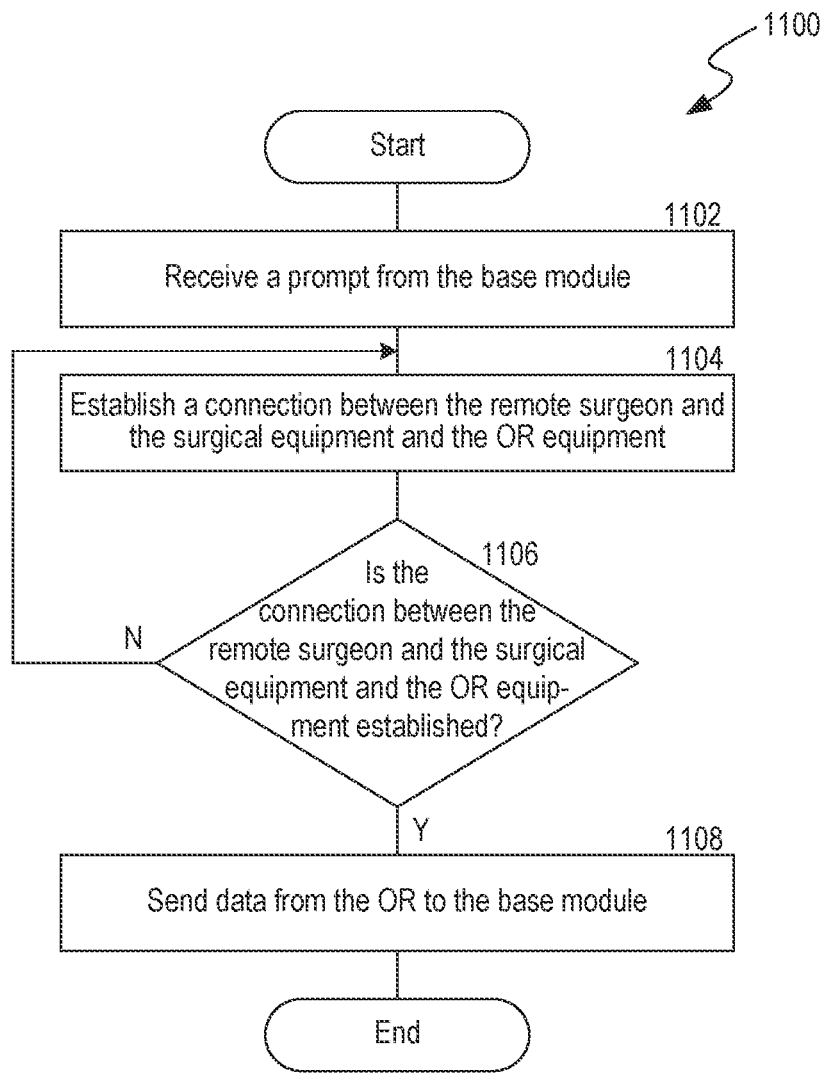
FIG. 11 is a flow diagram illustrating an example process for edge computing for robotic telesurgery using artificial intelligence, in accordance with one or more embodiments.

FIG. 11 is a flow diagram illustrating an example process 1100 for edge computing for robotic telesurgery using artificial intelligence, in accordance with one or more embodiments. In some embodiments, the process 1100 of FIG. 11 is performed by the remote surgeon module 630. The remote surgeon module 630 is illustrated and described in more detail with reference to FIG. 6. In other embodiments, the process 1100 of FIG. 11 is performed by a computer system, e.g., the example computer system 300 illustrated and described in more detail with reference to FIG. 3. Particular entities, for example, the console 108 or the robotic surgical system 160 perform some or all of the steps of the process 1100 in other embodiments. The console 108 and the robotic surgical system 160 are illustrated and described in more detail with reference to FIG. 1. Likewise, embodiments can include different and/or additional steps, or perform the steps in different orders.

In some alternative implementations, the functions noted in process 1100 occur out of the order noted in the drawings. For example, two steps shown in succession in FIG. 11 can in fact be executed substantially concurrently or the steps can sometimes be executed in the reverse order, depending upon the functionality involved. In addition, the process descriptions or steps in the flowchart can represent decisions made by a hardware structure such as a state machine.

In step 1102, the remote surgeon module 630 receives a prompt from the base module 626. The remote surgeon module 630 can receive a prompt to establish a connection between the remote surgeon and the equipment available at the surgeon's facility. In step 1104, the remote surgeon module 630 establishes a connection between a remote surgeon, the surgical robot 604, and the at least one OR equipment 612. The connection to the remote surgeon may be referred to as the connection with the remote surgeon equipment 620 or the remote surgeon computer 622, which can facilitate performance of the telesurgery procedure by the remote surgeon from a remote location. For example, the remote surgeon module 630 establishes a connection between the remote surgeon equipment 620, the remote surgeon computer 622 associated with Dr. T, the Surgical Drill 2 and a camera at the surgical facility in Chicago.

In step 1106, the remote surgeon module 630 determines whether the connection between the remote surgeon, the surgical robot 604, and the at least one OR equipment 612 is established. In one case, if the connection between the remote surgeon, the surgical robot 604, and the at least one OR equipment 612 is not established, then the remote surgeon module 630 moves to step 1104, to again establish the connection between the remote surgeon, the surgical robot 604, and the at least one OR equipment 612. For example, if the camera is not functional, then the remote surgeon module 630 again establishes the connection between the camera, the Surgical Drill 2, the remote surgeon equipment 620, and the remote surgeon computer 622 associated with Dr. T. In another case, if the connection between the remote surgeon, the surgical robot 604, and the at least one OR equipment 612 is established, then the remote surgeon module 630 moves to step 1108, to send data from the OR to the base module 626. In embodiments, the data from the OR can correspond to the surgical robot 604 and the at least one OR equipment 612. For example, the remote surgeon module 630 sends data from the camera and the Surgical Drill 2, with information related to the patient Alex, and his spinal fracture, to the base module 626.

Figure 12:
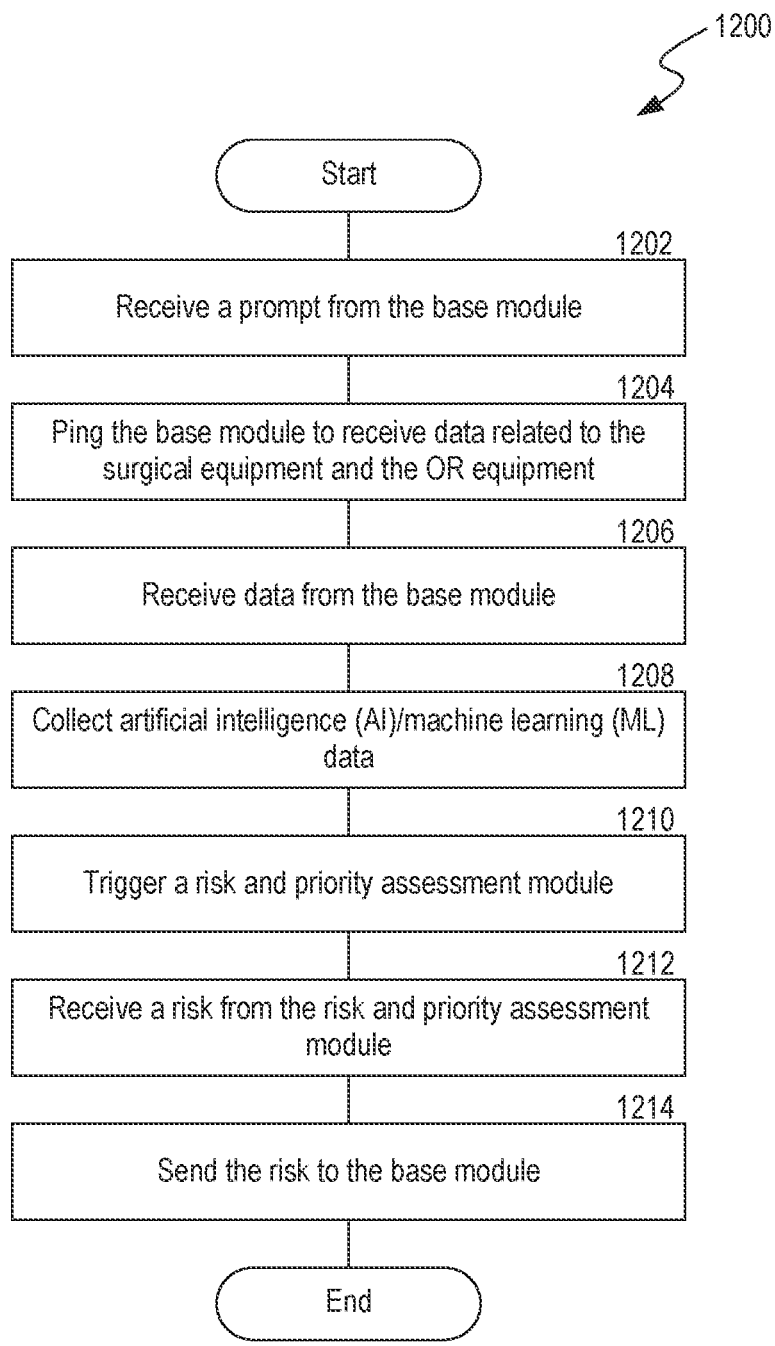
FIG. 12 is a flow diagram illustrating an example process for edge computing for robotic telesurgery using artificial intelligence, in accordance with one or more embodiments.

FIG. 12 is a flow diagram illustrating an example process 1200 for edge computing for robotic telesurgery using artificial intelligence, in accordance with one or more embodiments. In some embodiments, the process 1200 of FIG. 12 is performed by the operating workflow module 632. The operating workflow module 632 is illustrated and described in more detail with reference to FIG. 6. In other embodiments, the process 1200 of FIG. 12 is performed by a computer system, e.g., the example computer system 300 illustrated and described in more detail with reference to FIG. 3. Particular entities, for example, the console 108 or the robotic surgical system 160 perform some or all of the steps of the process 1200 in other embodiments. The console 108 and the robotic surgical system 160 are illustrated and described in more detail with reference to FIG. 1. Likewise, embodiments can include different and/or additional steps, or perform the steps in different orders.

In some alternative implementations, the functions noted in process 1200 occur out of the order noted in the drawings. For example, two steps shown in succession in FIG. 12 can in fact be executed substantially concurrently or the steps can sometimes be executed in the reverse order, depending upon the functionality involved. In addition, the process descriptions or steps in the flowchart can represent decisions made by a hardware structure such as a state machine.

In step 1202, the operating workflow module 632 receives a prompt from the base module 626. The operating workflow module 632 may receive a prompt to collect the data from an AI/ML module (e.g., the AI accelerator 636 or ML models 638) and analyze the risk associated with the currently used one or more OR equipment 612 and the surgical robot 604. In step 1204, the operating workflow module 632 pings the base module 626 to receive data related to the surgical robot 604 and the one or more OR equipment 612. The data related to the surgical robot 604 and the one or more OR equipment 612 may correspond to, but not be limited to, speed, torque, force, and temperature of the surgical robot 604 and information such as images, temperature of the surgical site of the patient, and information related to the surgical bed/table 612*e* of the patient.

In step 1206, the operating workflow module 632 receives data from the base module 626. The operating workflow module 632 receives the data related to the surgical robot 604. For example, the operating workflow module 632 receives the data respective to Surgical Drill 2, having a speed of 450 rpm, a torque of 43.4±6.3 Newton millimeter (N mm), a temperature of 42.6 degrees Celsius, and operating with a force of 2.2 N, and images from a camera corresponding to the 8th thoracic vertebra (T8) of Alex's spinal cord, and a temperature of the surgical facility in Chicago as 24 degrees Celsius.

In step 1208, based on the received data related to the surgical robot 604 and the one or more OR equipment 612, the operating workflow module 632 collects AI/ML data. In embodiments, the operating workflow module 632 collects AI/ML data from the edge computing system 610. The AI/ML data can be used for training of the ML model 638 (see FIG. 2). The AI/ML data can correspond to the analysis of raw data of the surgical robot 604 to provide instructions related to the telesurgery procedure being performed using the surgical robot 604. The AI/ML data can correspond to the correlation between various types of data to create a function to predict future adverse events in the telesurgery procedure. For example, if the surgical equipment being used for the procedure is Surgical Drill 2, having a speed of 450 rpm, a torque of 43.4±6.3 Newton millimeter (N mm), and a temperature of 42.6 degrees Celsius, operating with a force of 2.2 N, and images from the camera corresponding to the 8th thoracic vertebra (T8) of Alex's spinal cord, and the temperature of the surgical facility in Chicago is 24 degrees Celsius, the AI/ML data may correspond to an upcoming risk of the Surgical Drill 2 inserting a screw that touches the 9th thoracic vertebra (T9), causing pain to Alex. In step 1210, the operating workflow module 632 optionally triggers a risk and priority assessment module.

In step 1212, the operating workflow module 632 receives a predicted risk from a risk and priority assessment module. For example, the operating workflow module 632 receives an assessment that there is a risk that the Surgical Drill 2 may insert the screw at the 8th thoracic vertebra (T8) of Alex's spinal cord to touch the 9th thoracic vertebra (T9), causing pain to Alex. Successively, the operating workflow module 632 sends the risk prediction to the base module 626.

Figure 13:
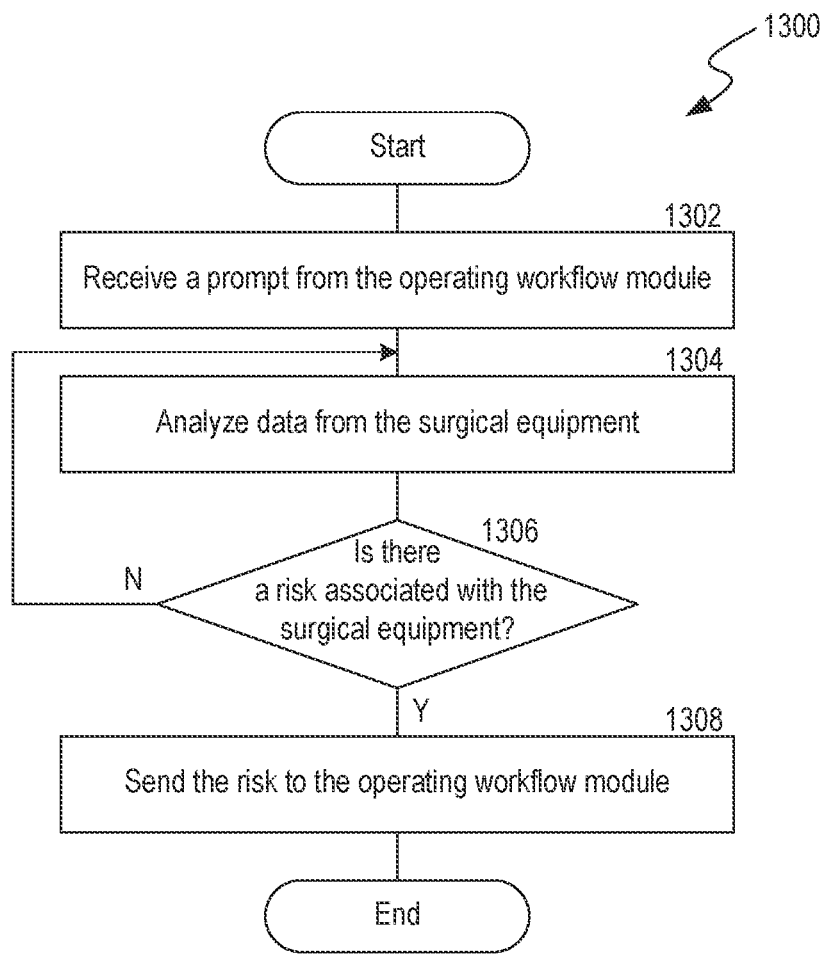
FIG. 13 is a flow diagram illustrating an example process for edge computing for robotic telesurgery using artificial intelligence, in accordance with one or more embodiments.

FIG. 13 is a flow diagram illustrating an example process for edge computing for robotic telesurgery using artificial intelligence, in accordance with one or more embodiments. In some embodiments, the process 1300 of FIG. 13 is performed by a risk and priority assessment module. The risk and priority assessment module can be implemented in the cloud or on the surgical robot 604, e.g., using the ML model 638. In other embodiments, the process 1300 of FIG. 13 is performed by a computer system, e.g., the example computer system 300 illustrated and described in more detail with reference to FIG. 3. Particular entities, for example, the console 108 or the robotic surgical system 160 perform some or all of the steps of the process 1300 in other embodiments. The console 108 and the robotic surgical system 160 are illustrated and described in more detail with reference to FIG. 1. Likewise, embodiments can include different and/or additional steps, or perform the steps in different orders.

In some alternative implementations, the functions noted in process 1300 occur out of the order noted in the drawings. For example, two steps shown in succession in FIG. 13 can in fact be executed substantially concurrently or the steps can sometimes be executed in the reverse order, depending upon the functionality involved. In addition, the process descriptions or steps in the flowchart can represent decisions made by a hardware structure such as a state machine.

In step 1302, the risk and priority assessment module receives a prompt from the operating workflow module 632. The operating workflow module 632 can receive a prompt to analyze the data received from the surgical robot 604. In step 1304, based on the received prompt from the operating workflow module 632, the risk and priority assessment module analyzes data from the surgical robot. For example, the risk and priority assessment module analyzes Surgical Drill 2, having a speed of 450 rpm, a torque of 43.4±6.3 Newton millimeter (N mm), and a temperature of 42.6 degrees Celsius, operating with a force of 2.2 N.

In step 1306, based on the analyzed data from the surgical robot 604, the risk and priority assessment module determines whether there is a risk associated with the surgical equipment (e.g., an adverse event). In one case, if there is no risk determined to be associated with the surgical robot 604, then the risk and priority assessment module moves to step 1304, to continue analyzing the data from the surgical robot 604. In another case, if the risk and priority assessment module determines that there is a risk associated with the surgical robot 604, then the risk and priority assessment module moves to step 1308, to send a determination of the risk or a prediction of the adverse event to the operating workflow module 632. For example, based on the analyzed data involving Surgical Drill 2, having a speed of 450 rpm, a torque of 43.4±6.3 Newton millimeter (N mm), and a temperature of 42.6 degrees Celsius, operating with a force of 2.2 N, the risk and priority assessment module determines that there is a risk that the Surgical Drill 2 may insert a screw at the 8th thoracic vertebra (T8) of Alex's spinal cord and touch the 9th thoracic vertebra (T9), causing pain to Alex, and sends this data to the operating workflow module 632.

Figure 14:
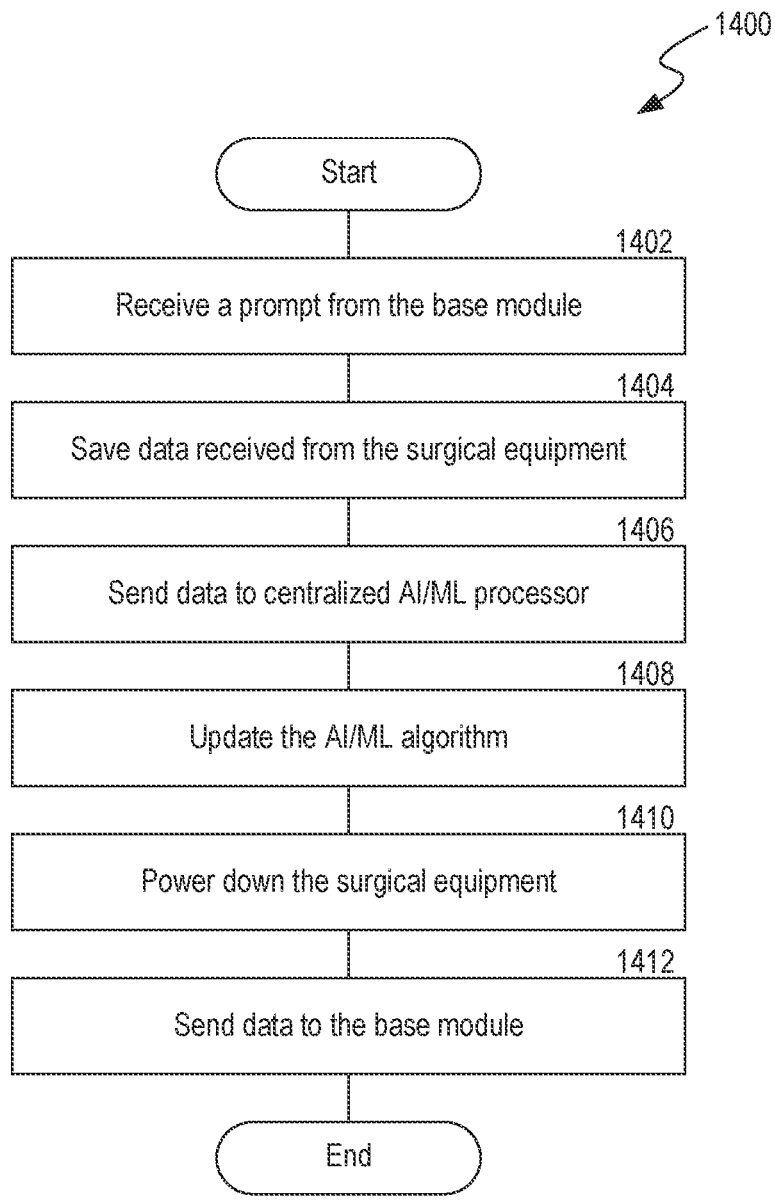
FIG. 14 is a flow diagram illustrating an example process for edge computing for robotic telesurgery using artificial intelligence, in accordance with one or more embodiments.

FIG. 14 is a flow diagram illustrating an example process 1400 for edge computing for robotic telesurgery using artificial intelligence, in accordance with one or more embodiments. In some embodiments, the process 1400 of FIG. 14 is performed by the end operating module 634. In other embodiments, the process 1400 of FIG. 14 is performed by a computer system, e.g., the example computer system 300 illustrated and described in more detail with reference to FIG. 3. Particular entities, for example, the console 108 or the robotic surgical system 160 perform some or all of the steps of the process 1400 in other embodiments. The console 108 and the robotic surgical system 160 are illustrated and described in more detail with reference to FIG. 1. Likewise, embodiments can include different and/or additional steps, or perform the steps in different orders.

In some alternative implementations, the functions noted in process 1400 occur out of the order noted in the drawings. For example, two steps shown in succession in FIG. 14 can in fact be executed substantially concurrently or the steps can sometimes be executed in the reverse order, depending upon the functionality involved. In addition, the process descriptions or steps in the flowchart can represent decisions made by a hardware structure such as a state machine.

In step 1402, the end operating module 634 receives a prompt from the base module 626, at step 1402. The end operating module 634 can update the AI/ML algorithm by training the ML models 638 to improve control of the surgical robot 604. In step 1404, the end operating module 634 saves the data received from the surgical robot 604. The data can be from, for example, one or more speed sensors, accelerometers, torque sensors, temperature sensors, force sensors, or the like. For example, the monitors 112 of FIG. 1 can include speed sensors, accelerometers, torque sensors, temperature sensors, force sensors, cameras, or other surgical robot sensors. The data can correspond to, but not be limited to, the speed, torque, temperature, and a force of the surgical robot 604. For example, the data may correspond to Surgical Drill 2, having a speed of 450 rpm, a torque of 43.4±6.3 Newton millimeter (N mm), and a temperature of 42.6 degrees Celsius, operating with a force of 2.2 N. The Surgical Drill 2 can include speed sensors, torque sensors, temperature sensors, and force sensors to provide such data. The number, configuration, and positions of the sensors can be selected and changed based on the data to be collected.

In step 1406, the end operating module 634 sends data to the AI accelerator 636. For example, the end operating module 634 sends data that corresponds to the Surgical Drill 2, having a speed of 450 rpm, a torque of 43.4±6.3 Newton millimeter (N mm), and a temperature of 42.6 degrees Celsius, operating with a force of 2.2 N. In step 1408, based on the sent data, the end operating module 634 updates the AI/ML algorithm and trains the ML models 638. The AI/ML algorithm is updated to reflect the instructions based on the updated data.

In step 1410, the end operating module 634 powers down the surgical equipment. For example, based on the received data related to the surgical robot 604, the end operating module 634 powers down the Surgical Drill 2 to avoid any pain to Alex. In embodiments, the robotic telesurgery system 600 is configured to perform at least one action by swapping a surgical drill for a spinal inserter. For example, the end operating module 634 switches from using the Surgical Drill 2 to the Spinal Surgery Robotic Arm Inserter-1, which presents fewer risks in a particular procedure as compared to the use of the Surgical Drill 2.

In step 1410, the end operating module 634 sends data to the base module 626. The end operating module 634 can send data related to the surgical robot 604 to the base module 626, for saving the data in the surgical equipment database 616 and the edge computing database 618. For example, the end operating module 634 sends data that the surgical robot 604 or the remote surgeon is switching from the Surgical Drill 2 to the Spinal Surgery Robotic Arm Inserter-1, which has fewer risks as compared to the use of the Surgical Drill-2.

The functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

The description and drawings herein are illustrative and are not to be construed as limiting. Numerous specific details are described to provide a thorough understanding of the disclosure. However, in certain instances, well-known details are not described in order to avoid obscuring the description. Further, various modifications can be made without deviating from the scope of the embodiments.

The terms used in this specification generally have their ordinary meanings in the art, within the context of the disclosure, and in the specific context where each term is used. Certain terms that are used to describe the disclosure are discussed above, or elsewhere in the specification, to provide additional guidance to the practitioner regarding the description of the disclosure. For convenience, certain terms can be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. One will recognize that "memory" is one form of a "storage" and that the terms can on occasion be used interchangeably.

Consequently, alternative language and synonyms can be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any term discussed herein is illustrative only and is not intended to further limit the scope and meaning of the disclosure or of any exemplified term. Likewise, the disclosure is not limited to various embodiments given in this specification.

It is to be understood that the embodiments and variations shown and described herein are merely illustrative of the principles of this invention and that various modifications can be implemented by those skilled in the art.

We claim:

1. A method for operating a surgical robotic system using edge computing, the method comprising:

causing, by a control system of a surgical robot, the surgical robot to robotically position one or more sensors to capture images of a surgical site, wherein the surgical robot comprises a robotic arm;

generating, by an artificial intelligence (AI) accelerator of the control system, a prediction of an adverse surgical event, using a machine learning (ML) model, based on the images of the surgical site received from the one or more sensors, the prediction indicating that insertion of a first implant would touch non-targeted tissue at the surgical site;

in response to the prediction of the adverse surgical event, transitioning control of the surgical robot to an edge computing system, wherein the edge computing system performs steps comprising:

generating, by the AI accelerator, instructions for controlling the surgical robot via the edge computing system to avoid the adverse surgical event during robotic surgery, wherein the AI accelerator of the edge computing system generates the prediction and the instructions on-the-edge while avoiding concurrent data transfer to a computer system over a network, and wherein the instructions direct insertion of a second implant different from the first implant to avoid touching the non-targeted tissue by the second implant;

moving, by robotic joints of the robotic arm, the robotic arm to perform robotic telesurgery, wherein the robotic arm is communicably coupled to the edge computing system;

positioning, by the surgical robot, the robotic arm in a configuration based on the instructions, the configuration defined by a spatial position and an orientation;

performing, by the surgical robot, at least one action to avoid the adverse surgical event when the robotic arm is positioned in the configuration;

determining the adverse surgical event was avoided by the surgical robot; and in response to determining the adverse surgical event was avoided, transitioning control of the surgical robot from the edge computing system to the control system.

2. The method of claim 1, wherein the surgical robot comprises a plurality of robotic arms, the method comprising:

coordinating motion for the plurality of robotic arms based on output of the edge computing system, wherein each robotic arm has one or more end effectors, and at least one of the end effectors is configured to perform the at least one action using at least one of a continuous-flow anesthesia machine, one or more surgical tools, one or more environment controls, or a motorized surgical bed.

3. The method of claim 1, wherein an end effector is configured to perform the at least one action using at least one of:
a drill, forceps, a scalpel, a retractor, a dilator, or a grasper; or a surgical tool, a gripping device, a probe, or an endoscope.

4. The method of claim 1, wherein the one or more sensors are further configured to measure at least one of:
a torque of the robotic arm;
temperature of an end effector; or
a power status of the surgical robot.

5. A surgical robotic system using edge computing, comprising:
a control system configured to:
cause a robotic arm of a surgical robot to robotically position one or more sensors to capture images of a surgical site;
generate, by an artificial intelligence (AI) accelerator, a prediction of an adverse surgical event, using a machine learning (ML) model, based on the images of the surgical site received from the one or more sensors, the prediction indicating that insertion of a first implant would touch non-targeted tissue at the surgical site;
in response to the prediction of the adverse surgical event, transitioning control of the surgical robot to an edge computing system, wherein the edge computing system is configured to:
generate instructions for controlling the robotic arm to avoid the adverse surgical event during robotic telesurgery, the instructions directing insertion of a second implant different from the first implant to avoid touching the non-targeted tissue by the second implant,
wherein the AI accelerator of the edge computing system generates the prediction and the instructions on-the-edge while avoiding concurrent data transfer to a computer system over a network;
move, by robotic joints of the robotic arm, the robotic arm to perform robotic telesurgery, wherein the robotic arm is communicably coupled to the edge computing system;
position the robotic arm in a configuration based on the instructions, the configuration defined by a spatial position and an orientation; and
perform at least one action to avoid the adverse surgical event when the robotic arm is positioned in the configuration;
determine the adverse surgical event was avoided by the surgical robot; and
in response to determining the adverse surgical event was avoided, transition control of the surgical robot from the edge computing system to the control system.

6. The surgical robotic system of claim 5, configured to perform the at least one action using at least one of a continuous-flow anesthesia machine, one or more surgical tools, one or more environment controls, or a motorized surgical bed.

7. The surgical robotic system of claim 5, configured to perform the at least one action using at least one of:
a drill, forceps, a scalpel, a retractor, a dilator, or a grasper; or a surgical tool, a gripping device, a probe, or an endoscope.

8. The surgical robotic system of claim 5, comprising the one or more sensors configured to measure at least one of:
a torque of the robotic arm;
a temperature of an end effector; or
a power status of the surgical robot.

9. The surgical robotic system of claim 5, wherein the one or more sensors comprise at least one of:
a global positioning system (GPS) receiver;
an infrared camera;
a wireless communication relay device; or
a laser sensor.

10. The surgical robotic system of claim 5, comprising one or more imaging devices, the one or more imaging devices comprising at least one of:
a magnetic resonance imaging (MRI) machine, an X-ray machine, or a camera,
wherein the one or more imaging devices are configured to capture the images of the surgical site.

11. The surgical robotic system of claim 5, configured to perform the at least one action by swapping a surgical drill for a spinal inserter.

12. The surgical robotic system of claim 5, configured to perform the at least one action while obviating transfer of data to a remote computer over the network.

13. A system comprising:
one or more computer processors; and
a non-transitory computer-readable storage medium storing computer instructions, which when executed by the one or more computer processors, cause the system to:
cause, by a control system, a surgical robot to robotically position one or more sensors to capture images of a surgical site, wherein the surgical robot comprises a robotic arm;
generate, by an artificial intelligence (AI) accelerator of the control system, a prediction of an adverse surgical event, using a machine learning (ML) model, based on images of a surgical site, the prediction indicating that insertion of a first implant would touch non-targeted tissue at the surgical site;
in response to the prediction of the adverse surgical event, transitioning control of the surgical robot to an edge computing system, wherein the edge computing system performs steps comprising:
generate, by the AI accelerator, instructions for controlling the surgical robot via the edge computing system to avoid the adverse surgical event during robotic telesurgery, the instructions directing insertion of a second implant different from the first implant to avoid touching the non-targeted tissue by the second implant,
wherein the AI accelerator of the edge computing system generates the prediction and the instructions on-the-edge while avoiding concurrent data transfer to a computer system over a network;
move, by robotic joints of the robotic arm, the robotic arm to perform the robotic telesurgery, wherein the robotic arm is communicably coupled to the edge computing system;
position, by the surgical robot, the robotic arm in a configuration based on the instructions, the configuration defined by a spatial position and an orientation; and perform, by the surgical robot, at least one action to avoid the adverse surgical event when the robotic arm is positioned in the configuration;

determine the adverse surgical event was avoided by the surgical robot; and in response to determining the adverse surgical event was avoided, transition control of the surgical robot from the edge computing system to the control system.

14. The system of claim 13, wherein the at least one action is performed using at least one of a continuous-flow anesthesia machine, one or more surgical tools, one or more environment controls, or a motorized surgical bed.

15. The system of claim 13, wherein the at least one action is performed using at least one of:
a drill, forceps, a scalpel, a retractor, a dilator, or a grasper; or
a surgical tool, a gripping device, a probe, or an endoscope.

16. The system of claim 13, wherein the one or more sensors are configured to measure at least one of:
a torque of the robotic arm;
temperature of an end effector; or
a power status of the surgical robot.

17. The system of claim 13, wherein the one or more sensors comprise at least one of:
a global positioning system (GPS) receiver;
an infrared camera,
a wireless communication relay device, or
a laser sensor.

18. The system of claim 13, wherein the one or more sensors comprise at least one of a magnetic resonance imaging (MRI) machine, an X-ray machine, or a camera.

19. The system of claim 13, wherein the computer instructions cause the system to perform the at least one action by swapping a surgical drill for a spinal inserter.

20. The system of claim 13, wherein the computer instructions cause the system to perform the at least one action while obviating transfer of data to a remote computer over the network.

21. The system of claim 13, wherein the computer instructions, which when executed by the one or more computer processors, cause the system to:
determine a plurality of surgical steps associated with a surgical plan to be performed by the surgical robot;
causing, by the control system, the surgical robot to perform a first surgical step of the plurality of surgical steps;
determining a second surgical step that avoids the predicted adverse surgical event and is compatible with subsequent surgical steps of the surgical plan; and
after transitioning control of the surgical robot to the edge computing system, causing, by the edge computing system, the surgical robot to perform the second surgical step to avoid the predicted adverse surgical event.

* * * * *